United States Patent
Baker et al.

(10) Patent No.: US 8,969,521 B2
(45) Date of Patent: Mar. 3, 2015

(54) GENERAL METHOD FOR DESIGNING SELF-ASSEMBLING PROTEIN NANOMATERIALS

(71) Applicants: University of Washington through its Center for Commercialization, Seattle, WA (US); The Regents of the University of California, Oakland, CA (US)

(72) Inventors: David Baker, Seattle, WA (US); Neil King, Seattle, WA (US); William Sheffler, Seattle, WA (US); Todd Yeates, Agoura Hills, CA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 0 days.

(21) Appl. No.: 13/802,464

(22) Filed: Mar. 13, 2013

(65) Prior Publication Data

US 2013/0274441 A1     Oct. 17, 2013

Related U.S. Application Data

(60) Provisional application No. 61/622,889, filed on Apr. 11, 2012.

(51) Int. Cl.
| | |
|---|---|
| C07K 1/00 | (2006.01) |
| C07H 21/02 | (2006.01) |
| C12N 1/20 | (2006.01) |
| C12N 15/00 | (2006.01) |
| G06F 19/12 | (2011.01) |
| G06F 19/16 | (2011.01) |

(52) U.S. Cl.
CPC ............... *G06F 19/12* (2013.01); *G06F 19/16* (2013.01)
USPC ..................... 530/350; 536/23.1; 435/252.33; 435/320.1

(58) Field of Classification Search
CPC ........ A61K 38/00; C07K 14/47; C07H 21/00; C12N 15/70
USPC ........... 435/252.33, 320.1; 530/350; 536/23.1
See application file for complete search history.

(56) References Cited

FOREIGN PATENT DOCUMENTS

WO    WO2013056122 A1 *  4/2013

OTHER PUBLICATIONS

McCoy, et al. Phaser crystallographic software. J Appl Crystallogr 40, 658-674 (2007).
Crowley, et al. Structural insight into the mechanisms of transport across the *Salmonella enterica* Pdu microcompartment shell. J. Biol. Chem. 285, 37838-46 (2010).
Murshudov, A. A. Vagin, E. J. Dodson. Refinement of macromolecular structures by the maximum-likelihood method. Acta Crystallogr. D Biol. Crystallogr. 53, 240-55 (1997).
Blanc, et al. Refinement of severely incomplete structures with maximum likelihood in BUSTER-TNT. Acta Crystallogr. D Biol. Crystallogr. 60, 2210-21 (2004).
Winn, G. N. Murshudov, M. Z. Papiz. Macromolecular TLS refinement in REFMAC at moderate resolutions. Meth. Enzymol. 374, 300-21 (2003).
Emsley, B. Lohkamp, W. G. Scott, K. Cowtan. Features and development of Coot. Acta Crystallogr. D Biol. Crystallogr. 66, 486-501 (2010).
Laskowski, M. W. MacArthur, D. S. Moss, J. M. Thornton. PROCHECK: a program to check the stereochemical quality of protein structures. J. Appl. Cryst. 26, 283-291 (1993).
Colovos, T. O. Yeates. Verification of protein structures: patterns of nonbonded atomic interactions. Protein Sci. 2, 1511-9 (1993).
Lüthy, J. U. Bowie, D. Eisenberg. Assessment of protein models with three-dimensional profiles. Nature 356, 83-5 (1992).
Lanci, et al. Computational Design of a protein crystal. PNAS, 109(19): 7304-7309 (2012).
King, et al. Computational Design of Self-Assembling Protein Nanomaterials with Atomic Level Accuracy. Science, 336, 1171-1174 (2012).
Das, et al. Simultaneous prediction of protein folding and docking at high resolution. PNAS, 106(45):18978-18983 (2009).
Seeman. Nanomaterials based on DNA. Annu. Rev. Biochem. 79, 65-87 (2010).
Rothemund. Folding DNA to create nanoscale shapes and patterns. Nature 440, 297-302 (2006).
Andersen, et al. Self-assembly of a nanoscale DNA box with a controllable lid. Nature 459, 73-6 (2009).
Zheng, et al. From molecular to macroscopic via the rational design of a self-assembled 3D DNA crystal. Nature 461, 74-7 (2009).
Zhang. Fabrication of novel biomaterials through molecular self-assembly. Nat. Biotechnol. 21, 1171-8 (2003).
Douglas, M. Young. Viruses: making friends with old foes. Science 312, 873-5 (2006).
Lovejoy, et al. Crystal structure of a synthetic triple-stranded alpha-helical bundle. Science 259, 1288-93 (1993).
Harbury, J. J. Plecs, B. Tidor, T. Alber, P. S. Kim. High-resolution protein design with backbone freedom. Science 282, 1462-7 (1998).
Gribbon, et al. MagicWand: a single, designed peptide that assembles to stable, ordered alpha-helical fibers. Biochemistry 47, 10365-71 (2008).

(Continued)

*Primary Examiner* — David J Steadman
*Assistant Examiner* — Paul Holland
(74) *Attorney, Agent, or Firm* — McDonnell Boehnen Hulbert & Berghoff LLP

(57) ABSTRACT

Methods and systems for computationally designing self-assembling polypeptides are disclosed. A representation of a docked configuration of a symmetric protein architecture can be determined by a computing device configured to computationally symmetrically dock representations of protein building blocks within a representation of a symmetric protein architecture, where symmetrically docking a representation of a particular protein building block can include determining a configuration of the protein building blocks in three-dimensional space within the symmetric protein architecture configured to generate interfaces between building blocks suitable for computational protein interface design. The amino acid sequence of the docked protein building blocks can be computationally modified to specify protein-protein interfaces between the plurality of protein building blocks that are energetically favorable to drive self-assembly of a protein that includes the modified amino acid sequence.

20 Claims, 13 Drawing Sheets

(56) References Cited

OTHER PUBLICATIONS

Zaccai, et al. A de novo peptide hexamer with a mutable channel. Nat. Chem. Biol. 7, 935-41 (2011).

Koder, et al. Design and engineering of an O(2) transport protein. Nature 458, 305-9 (2009).

Ballister, A. H. Lai, R. N. Zuckermann, Y. Cheng, J. D. Mougous. In vitro self-assembly of tailorable nanotubes from a simple protein building block. Proc. Natl. Acad. Sci. U.S.A. 105, 3733-8 (2008).

Usui, et al. Nanoscale elongating control of the self-assembled protein filament with the cysteine-introduced building blocks. Protein Sci. 18, 960-9 (2009).

Ringler, G. E. Schulz. Self-assembly of proteins into designed networks. Science 302, 106-9 (2003).

Salgado, J. Faraone-Mennella, F. A. Tezcan. Controlling protein-protein interactions through metal coordination: assembly of a 16-helix bundle protein. J. Am. Chem. Soc. 129, 13374-5 (2007).

Salgado, R. J. Radford, F. A. Tezcan. Metal-directed protein self-assembly. Acc. Chem. Res. 43, 661-72 (2010).

Grigoryan, et al. Computational design of virus-like protein assemblies on carbon nanotube surfaces. Science 332, 1071-6 (2011).

Padilla, C. Colovos, T. O. Yeates. Nanohedra: using symmetry to design self assembling protein cages, layers, crystals, and filaments. Proc. Natl. Acad. Sci. U.S.A. 98, 2217-21 (2001).

Sinclair, K. M. Davies, C. Vénien-Bryan, M. E. Noble. Generation of protein lattices by fusing proteins with matching rotational symmetry. Nat. Nanotechnol. 6, 558-62 (2011).

Janin, R. P. Bahadur, P. Chakrabarti. Protein-protein interaction and quaternary structure. Q. Rev. Biophys. 41, 133-80 (2008).

Grueninger, et al. Designed protein-protein association. Science 319, 206-9 (2008).

Kortemme, et al. Computational redesign of protein-protein interaction specificity. Nat. Struct. Mol. Biol. 11, 371-9 (2004).

Huang, J. J. Love, S. L. Mayo. A de novo designed protein protein interface. Protein Sci. 16, 2770-4 (2007).

Jha, et al. Computational design of a PAK1 binding protein. J. Mol. Biol. 400, 257-70 (2010).

Karanicolas, et al. A de novo protein binding pair by computational design and directed evolution. Mol. Cell 42, 250-60 (2011).

Stranges, M. Machius, M. J. Miley, A. Tripathy, B. Kuhlman. Computational design of a symmetric homodimer using β-strand assembly. Proc. Natl. Acad. Sci. U.S.A. 108, 20562-7 (2011).

Fleishman, et al. Computational design of proteins targeting the conserved stem region of influenza hemagglutinin. Science 332, 816-21 (2011).

Fleishman, et al. Hotspot-centric de novo design of protein binders. J. Mol. Biol. 413, 1047-62 (2011).

Kuhlman, D. Baker. Native protein sequences are close to optimal for their structures. Proc. Natl. Acad. Sci. U.S.A. 97, 10383-8 (2000).

DiMaio, A. Leaver-Fay, P. Bradley, D. Baker, I. André. Modeling symmetric macromolecular structures in Rosetta3. PLoS One 6, e20450 (2011).

Cooper, F. et al. Predicting protein structures with a multiplayer online game. Nature 466, 756-60 (2010).

Zhou, et al. Genetically encoded short peptide tags for orthogonal protein labeling by Sfp and AcpS phosphopantetheinyl transferases. ACS Chem. Biol. 2, 337-46 (2007).

Krissinel, K. Henrick. Inference of macromolecular assemblies from crystalline state. J. Mol. Biol. 372, 774-97 (2007).

Levy, J. B. Pereira-Leal, C. Chothia, S. A. Teichmann. 3D complex: a structural classification of protein complexes. PLoS Comput. Biol. 2, e155 (2006).

Fleishman, et al. Community-wide assessment of protein-interface modeling suggests improvements to design methodology. J. Mol. Biol. 414, 289-302 (2011).

Lawrence, P. M. Colman. Shape complementarity at protein/protein interfaces. J. Mol. Biol. 234, 946-50 (1993).

Sheffler, D. Baker. RosettaHoles2: a volumetric packing measure for protein structure refinement and validation. Protein Sci. 19, 1991-5 (2010).

Fleishman, S. D. Khare, N. Koga, D. Baker. Restricted sidechain plasticity in the structures of native proteins and complexes. Protein Sci. 20, 753-7 (2011).

Prodromou, L. H. Pearl. Recursive PCR: a novel technique for total gene synthesis. Protein Eng. 5, 827-9 (1992).

Schuck. Size-distribution analysis of macromolecules by sedimentation velocity ultracentrifugation and lamm equation modeling. Biophys. J. 78, 1606-19 (2000).

Ohi, Y. Li, Y. Cheng, T. Walz. Negative staining and image classification—powerful tools in modern electron microscopy. Biol Proced Online 6, 23-34 (2004).

Smith J. XIMDISP—A visualization tool to aid structure determination from electron microscope images. J. Struct. Biol. 125, 223-228 (1999).

van Heel, G. Harauz, E. V. Orlova, R. Schmidt, M. Schatz. A new generation of the IMAGIC image processing system. J. Struct. Biol. 116, 17-24 (1996).

Mindell, N. Grigorieff. Accurate determination of local defocus and specimen tilt in electron microscopy. J. Struct. Biol. 142, 334-47 (2003).

Ludtke, P. R. Baldwin, W. Chiu. EMAN: semiautomated software for high-resolution single-particle reconstructions. J. Struct. Biol. 128, 82-97 (1999).

Grigorieff. FREALIGN: high-resolution refinement of single particle structures. J. Struct. Biol. 157, 117-25 (2007).

Pettersen, et al. UCSF Chimera—a visualization system for exploratory research and analysis. J Comput Chem 25, 1605-12 (2004).

Tsai, M. R. Sawaya, T. O. Yeates. Analysis of lattice-translocation disorder in the layered hexagonal structure of carboxysome shell protein CsoS1C. Acta Crystallogr. D Biol. Crystallogr. 65, 980-8 (2009).

Otwinowski, W. Minor. Processing of X-ray diffraction data collected in oscillation mode. Methods in Enzymology 276, Macromolecular Crystallography, part A (C.W. Carter, Jr., R. M. Sweet, Eds., Academic Press New York), 307-326, 1997.

Kabsch. XDS. Acta Cryst. D 66, 125-132 (2010).

\* cited by examiner

GENERAL METHOD FOR DESIGNING SELF-ASSEMBLING PROTEIN NANOMATERIALS

CROSS-REFERENCE TO RELATED APPLICATIONS

Coordinates for each of the 271 proteins were downloaded from the Protein Data Bank, the trimeric axis was aligned along the vector [0,0,1], and the center of mass of the trimer translated to the origin. A single subunit of each trimer was used as input into our design protocol without further modification.

BACKGROUND OF THE INVENTION

Unless otherwise indicated herein, the materials described in this section are not prior art to the claims in this application and are not admitted to be prior art by inclusion in this section.

Molecular self-assembly is an elegant and powerful approach to patterning matter on the atomic scale. Recent years have seen advances in the development of self-assembling biomaterials, particularly those composed of nucleic acids. DNA has been used to create, for example, nanoscale shapes and patterns, molecular containers, and three-dimensional macroscopic crystals. Methods for designing self-assembling proteins have progressed more slowly, yet the functional and physical properties of proteins make them attractive as building blocks for the development of advanced functional materials.

In any self-assembling structure, interactions between the subunits are required to drive assembly. Previous approaches to designing self-assembling proteins have satisfied this requirement in various ways, including the use of relatively simple and well-understood coiled-coil and helical bundle interactions, engineered disulfide bonds, chemical cross-links, metal-mediated interactions, templating by non-biological materials in conjunction with computational protein interface design, or genetic fusion of multiple protein domains or fragments which naturally self-associate.

In some scenarios, computational modeling and design of molecules can aid researchers in investigating the molecules. For example, computational protein design can provide valuable reagents for biomedical and biochemical research, identify sequences compatible with a given protein backbone, and design protein folds.

SUMMARY

In one aspect, a method of designing self-assembling polypeptides is provided. A computing device generates a representation for each protein building block of a plurality of protein building blocks and a representation for a symmetric protein architecture. The computing device determines a representation of a docked configuration of the symmetric protein architecture by computationally symmetrically docking each representation of the plurality of representations of protein building blocks within the representation of the symmetric protein architecture. Computationally symmetrically docking a representation of a particular protein building block within the representation of the symmetric protein architecture includes computationally determining a configuration of the plurality of protein building blocks in three-dimensional space within the symmetric protein architecture configured for generating interfaces between each building block that are suitable for computational protein interface design. The computing device computationally modifies an amino acid sequence of docked protein building blocks to specify representations of protein-protein interfaces between the plurality of protein building blocks that are energetically favorable to drive self-assembly of a protein that includes the modified amino acid sequence to the docked configuration. The computing device generates an output that is based on at least one representation of the group consisting of the representation of the docked configuration of the symmetric protein architecture, the representations of protein-protein interfaces between the plurality of protein building blocks that is energetically favorable to drive self-assembly of a protein, and a representation of the protein comprising the modified amino acid sequence to the docked configuration.

In another aspect, a computing device is provided. The computing device includes a process and data storage. The data storage, having stored therein computer-readable program instructions that, upon execution by the processor, cause the computing device to perform functions. The functions include generating a representation for each protein building block of a plurality of protein building blocks and a representation for a symmetric protein architecture; determining a representation of a docked configuration of the symmetric protein architecture by computationally symmetrically docking each representation of the plurality of representations of protein building blocks within the representation of the symmetric protein architecture, where computationally symmetrically docking a representation of a particular protein building block within the representation of the symmetric protein architecture includes computationally determining a configuration of the plurality of protein building blocks in three-dimensional space within the symmetric protein architecture configured for generating interfaces between each building block that are suitable for computational protein interface design; computationally modifying an amino acid sequence of docked protein building blocks to specify representations of protein-protein interfaces between the plurality of protein building blocks that are energetically favorable to drive self-assembly of a protein comprising the modified amino acid sequence to the docked configuration; and generating an output based on at least one representation of the group consisting of the representation of the docked configuration of the symmetric protein architecture, the representations of protein-protein interfaces between the plurality of protein building blocks that is energetically favorable to drive self-assembly of a protein, and a representation of the protein comprising the modified amino acid sequence to the docked configuration.

In yet another aspect, a non-transitory computer readable storage medium is provided. The non-transitory computer readable storage medium, having stored thereon computer-readable program instructions that, upon execution by a processor, cause the processor to perform functions. The functions include generating a representation for each protein building block of a plurality of protein building blocks and a representation for a symmetric protein architecture; determining a representation of a docked configuration of the symmetric protein architecture by computationally symmetrically docking each representation of the plurality of representations of protein building blocks within the representation of the symmetric protein architecture, where computationally symmetrically docking a representation of a particular protein building block within the representation of the symmetric protein architecture includes computationally determining a configuration of the plurality of protein building blocks in three-dimensional space within the symmetric protein architecture configured for generating interfaces between each building block that are suitable for computational protein interface design; computationally modifying an amino acid sequence of docked protein building blocks to specify representations of protein-protein interfaces between the plurality of protein building blocks that are energetically favorable to drive self-assembly of a protein comprising the modified amino acid sequence to the docked configuration; and generating an output based on at least one representation of the group consisting of the representation of the docked configuration of the symmetric protein architecture, the representations of protein-protein interfaces between the plurality of protein building blocks that is energetically favorable to drive self-assembly of a protein, and a representation of the protein comprising the modified amino acid sequence to the docked configuration.

In a further aspect, the present invention provides isolated polypeptides, comprising the amino acid sequence of SEQ ID NO:1, wherein any defined residue can be modified by a conservative amino acid substitution, and wherein the polypeptide does not comprise the amino acid sequence of SEQ ID NO: 7. In one embodiment, the polypeptide comprises the amino acid sequence of SEQ ID NO:1. In another embodiment, the polypeptide comprises the amino acid sequence of SEQ ID NO:2. In another embodiment, the invention provides multimeric assemblies, comprising a plurality of identical polypeptides monomers according to SEQ ID NO:1.

In a further aspect, the present invention provides isolated polypeptides, comprising the amino acid sequence of SEQ ID NO:3, wherein any defined residue can be modified by a conservative amino acid substitution, and wherein the polypeptide does not comprise the amino acid sequence of SEQ ID NO: 8. In one embodiment, the polypeptide comprises the amino acid sequence of SEQ ID NO:3. In another embodiment, the polypeptide comprises an amino acid sequence selected from the group consisting of SEQ ID NO:4, SEQ ID NO:5, and SEQ ID NO:6. In another embodiment, the invention provides multimeric assemblies, comprising a plurality of identical polypeptides monomers according to SEQ ID NO:3.

In another aspect, the present invention provides isolated nucleic acids encoding the polypeptide of the invention. In a further aspect, the invention provides nucleic acid expression vectors comprising an isolated nucleic acid of the invention. In another aspect, the present invention provides recombinant host cells, comprising a nucleic acid expression vector according to the invention.

DETAILED DESCRIPTION

Figure 1:
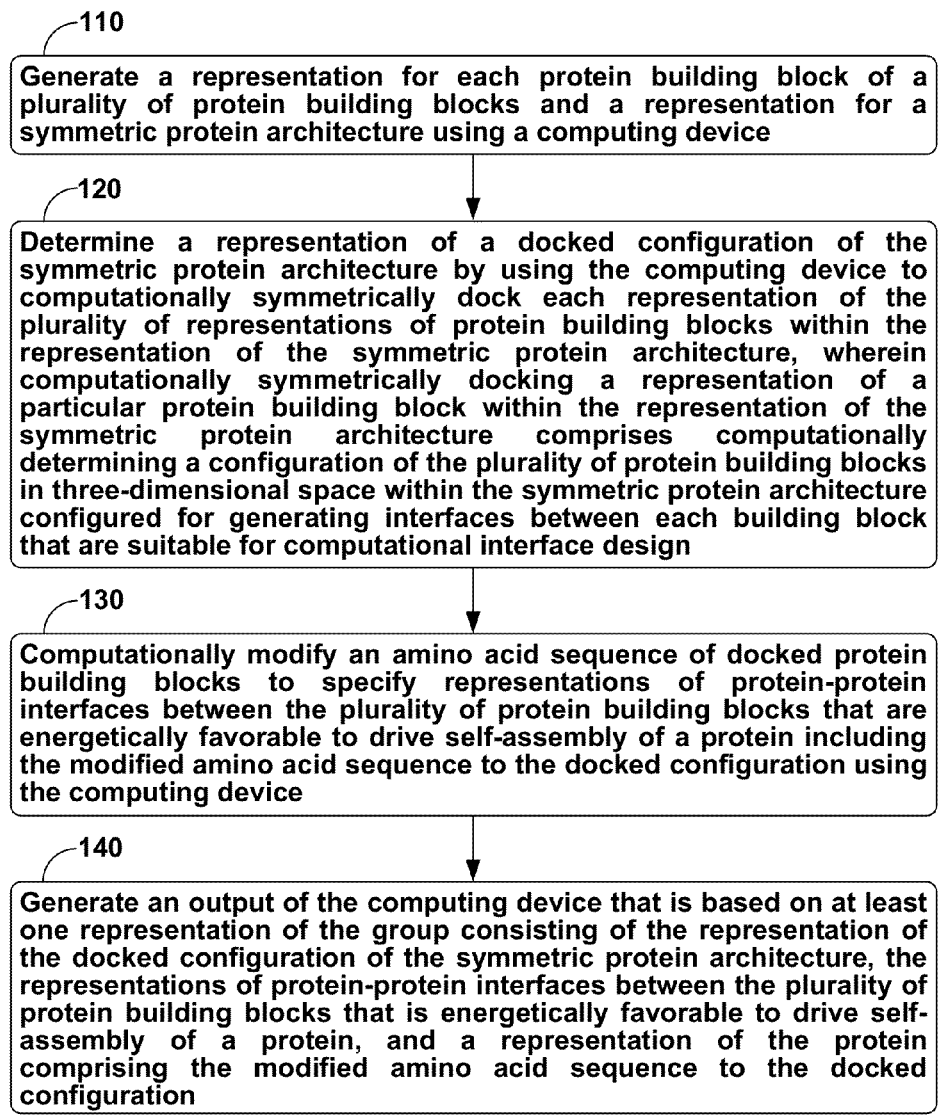
FIG. 1 is a flow chart of an example method.

Natural protein assemblies are most often held together by many weak, noncovalent interactions which together form large, highly complementary, low energy protein-protein interfaces. Such interfaces spontaneously self-assemble and allow precise definition of the orientation of subunits relative to one another, which is critical for obtaining the desired material with high accuracy. Designing assemblies with these properties has been difficult due to the complexities of modeling protein structures and energetics. For instance, a pioneering study used interface design by visual inspection to design new oligomeric structures, yet the experimentally determined dimeric interfaces were largely unanticipated. However, recent advances, including the de novo design of a heterodimeric protein interface with atomic level accuracy, suggest that our ability to computationally model and design protein-protein interactions is rapidly maturing.

A general computational method for designing self-assembling protein materials is disclosed, involving two techniques: 1) symmetrical docking of protein building blocks in a target symmetric architecture followed by 2) design of low energy protein-protein interfaces between the building blocks to drive self-assembly. As an example, oligomeric proteins that share an element of symmetry with the target architecture are used as building blocks.

As a proof of concept the method was used to design cage-like or shell-like protein nanomaterials having cage-like or shell-like structures with either tetrahedral (T) or octahedral (O) point group symmetry. An assembly with symmetry T uses 12 copies of a protein molecule arranged in 12 symmetry-related orientations, whereas symmetry O uses 24 molecules. Both point groups can be generated from sets of three-fold rotational symmetry axes, allowing the use of protein trimers with C3 symmetry as building blocks; in each case, only a single new interface between the trimeric building blocks is used for self-assembly. As an example, 271 naturally trimeric protein structures were docked symmetrically in both the tetrahedral and octahedral target architectures by aligning the three-fold axis of each building block with the three-fold axes in the target architecture and then systematically sampling the two remaining rigid body degrees of freedom, radial displacement and axial rotation, in increments of 1 Å and 1°, respectively.

In a similar manner, cages with icosahedral symmetry or a number of other symmetries can be designed using monomeric or oligomeric protein building blocks. In addition, all three point groups can be built from sets of two-fold rotational symmetry axes, allowing the use of protein dimers with C2 symmetry as building blocks; in each case, only a single new interface between the dimeric building blocks is used for self-assembly. In some embodiments, the cage-like or shell-like structure of a protein nanomaterial in a docked configuration can enclose one or more molecules, which may be unrelated to the protein nanomaterial. In other embodiments, the one or more molecules can be displayed on a surface of the cage-like or shell-like structure.

For each docked configuration in which no clashes between the backbone and beta carbon atoms of adjacent building blocks were present, a simple proxy for interface size and complementarity was computed to gauge the "designability" of the configuration. Around each of the 10 octahedral or 20 tetrahedral most designable configurations for each building block, a set of input structures for design was generated by sampling the radial displacement and axial rotation of the subunits more finely (0.1 Å, 0.5°).

For these input structures, symmetric RosettaDesign calculations using the Rosetta software suite of protein design programs can be used to design new amino acid sequences for the protein with in low-energy, symmetric protein-protein interactions between the trimeric building blocks. For example, revision 42921 of the Rosetta software suite can be used. Designs with the lowest predicted binding energies and geometrically complementary interfaces of sufficient size were further optimized using RosettaDesign and interactive design using a foldit program of the Rosetta software suite. 8 tetrahedral and 33 octahedral designs derived from 15 distinct natural trimeric proteins, containing on average 9 mutations per monomer, were selected for experimental characterization.

The herein-described methods and techniques are not limited to use of RosettaDesign, the Rosetta software suite, or any other specific software package. For example, other software programs could be used in conjunction with this method to design new amino acid sequences at the protein-protein interface.

Genes encoding the designed proteins and the corresponding wild-type trimers were constructed and cloned into an expression vector that appended an 11-residue peptide substrate for fluorescent modification by the *E. coli* acyl-carrier protein synthase AcpS. *E. coli* cells expressing the proteins were lysed, the proteins were fluorescently labeled in the clarified lysates by the addition of AcpS and the CoA-488 fluorophore, and the apparent size of each protein was visualized by subjecting the labeled lysates to PAGE under nondenaturing (native) conditions. Out of 7 T and 17 O designs that expressed solubly, one designed protein of each architecture revealed a shift in apparent size relative to the corresponding wild-type trimer that suggested self-assembly to the desired material. Size exclusion chromatography (SEC) of the labeled lysates confirmed the change in apparent molecular weight for the two designs. Genes encoding the octahedral design ("O3-33"; 9 mutations from the wild-type protein), the tetrahedral design ("T3-08"; 8 mutations), and the corresponding wild-type trimeric proteins were then subcloned into an expression vector that appended C-terminal $(His)_6$ tags, after which the proteins were expressed and purified by nickel affinity chromatography and SEC.

The designed protein O3-33 eluted from the SEC column as a single peak with an apparent size of about 24 subunits. The wild-type protein from which O3-33 was derived (PDB ID 3N79) did not assemble to a higher order structure; it eluted from the column mostly as trimers, with a small peak corresponding to a dimer of trimers. Analytical ultracentrifugation revealed that the designed protein sedimented as a single discrete species with a Stokes radius of 7.3 nm, in close agreement with the radius of the designed 24-subunit assembly. A point mutation (Ala167Arg) that introduced unfavorable steric clashes at the designed interface disrupted the material, suggesting that the observed self-assembly is due to the designed interface. Negative stain electron microscopy (EM) of O3-33 revealed fields of monodisperse particles of the expected size (~13 nm), many of which strikingly resembled projections of the design model along its 2-fold, 3-fold, or 4-fold symmetry axes. A single particle reconstruction of O3-33 obtained by EM analysis under cryogenic conditions clearly recapitulated the architecture of the design model, verifying that the protein assembles in solution as designed.

Crystal structures of O3-33 were solved to evaluate the accuracy of the design protocol at high resolution. Structures from two different crystal forms confirmed that the designed material adopts the target architecture and that the designed interface is responsible for driving self-assembly. The structure proved remarkably similar to the design model: the backbone RMSD over all 24 chains is 1.07 Å, and is lower if calculated using only the residues at the interface (0.85 Å). The high resolution of the structure allowed confident determination of the side chain configurations at the designed interface, revealing that the atomic contacts closely match those in the design model. The asymmetric unit of the designed interface consists of one alpha helix packing against a beta strand, a loop, and the symmetrically related helix in a neighboring building block. Several ordered water molecules were resolved at the designed interface that contribute bridging hydrogen-bonding interactions between neighboring building blocks. Truncation of designed interface residues to alanine disrupted octahedral self-assembly. For example, the Ser156Ala mutation, which alters O3-33 by the removal of only two atoms out of 2,827 total atoms in the subunit, significantly impaired assembly. This result underscores the importance of both the detailed atomic contacts designed by our protocol and the multiplicative effect of the symmetry of the system: the Ser156Ala mutation results in the loss of 24 interface hydrogen bonds in the fully assembled material.

The designed protein T3-08 appeared by SEC to be in a slow equilibrium between two states comprising three and approximately 12 subunits. The corresponding wild-type trimeric protein (PDB ID 3FTT) eluted from the column as trimer only. Disruption of the designed interface by a point mutation, Ala52Gln, again suggested that the designed interface is responsible for the observed self-assembly. A crystal structure of T3-08 revealed that the protein assembles to the desired tetrahedral architecture, but the trimeric building blocks are slightly rotated about the shared trimeric/tetrahedral three-fold rotational axes, subtly altering the atomic contacts at the designed interface relative to the design model and resulting in a backbone RMSD of 2.66 Å over all 12 subunits.

Two additional variants of T3-08 were designed in order to determine whether the designed configuration could be preferentially stabilized relative to the unanticipated configuration observed in the T3-08 crystal structure. One of the variants, T3-10, which contained 3 mutations relative to T3-08 intended to provide better hydrophobic packing near the tetrahedral three-fold interface, was purified by nickel affinity chromatography and appeared by SEC to self-assemble efficiently to the tetrahedral state, yielding little detectable trimer. Negative stain EM images of T3-10 revealed monodisperse particles of the expected size (~11 nm), averages of which closely resembled projections of the design model along its 2-fold and 3-fold symmetry axes. A crystal structure of T3-10 verified that the original designed configuration was stabilized as intended; the backbone RMSD between the T3-10 crystal structure and the T3-08/T3-10 design models is 0.62 Å. As observed for O3-33, the atomic contacts at the designed interface, which consists of two alpha helices and two short loops, closely match those in the design model. This result illustrates how small alterations to the protein sequence at the designed interface may allow fine control over the structure of the resulting material.

The herein-disclosed methods, strategies and techniques can enable high-accuracy design of self-assembling protein materials. The herein-disclosed design strategy comprising combining symmetrical docking with interface design, is conceptually simple and generally applicable to the design of a broad range of symmetric materials. In addition to the finite, cage-like or shell-like materials described here, unbounded materials in one, two, or three dimensions (i.e., fibers/helices, layers, or crystals) may be designed by choosing an appropriate target symmetric architecture. Although in the present study we used naturally occurring oligomeric proteins as building blocks, novel oligomeric building blocks could first be designed from monomers and after structural validation, used in the design of higher order assemblies with the attendant advantages of hierarchical assembly, or, with improvements in our symmetrical docking protocol, larger self-assembling systems could be designed directly from monomeric building blocks. The atomic-level accuracy of our designed materials demonstrates that using designed protein-protein interfaces to drive self-assembly results in highly ordered materials with superior rigidity and monodispersity. With further development, designed self-assembling protein materials similar to those described here could form the basis of advanced functional materials and custom-designed molecular machines with wide-ranging applications.

Example Operations

FIG. 1 is a flow chart of an example method 100. Method 100 can begin at block 110, where a computing device, such as computing device 1000 described below in the context of at least FIG. 10A, can generate a representation for each protein building block of a plurality of protein building blocks and a representation for a symmetric protein architecture. In some embodiments, each of the plurality of protein building blocks can include a protein that shares an element of symmetry with the symmetric protein architecture.

In other embodiments, each of the protein building blocks can include a naturally occurring oligomeric polypeptide. In still other embodiments, each of the protein building blocks can include a synthetic polypeptide.

In yet other embodiments, the symmetric protein architecture can conform to a symmetry selected from the group of symmetries consisting of a cyclic point group symmetry, a dihedral point group symmetry, a cubic point group symmetry, a line group symmetry, a plane group symmetry, a layer group symmetry, and a space group symmetry.

At block 120, the computing device can determine a representation of a docked configuration of the symmetric protein architecture by computationally symmetrically docking each representation of the plurality of representations of protein building blocks within the representation of the symmetric protein architecture. Computationally symmetrically docking a representation of a particular protein building block within the representation of the symmetric protein architecture can include computationally determining a configuration of the plurality of protein building blocks in three-dimensional space within the symmetric protein architecture configured for generating interfaces between each building block that are suitable for computational protein interface design.

In some embodiments, each of the protein building blocks can include a symmetry axis. Then, using the computing device to computationally symmetrically dock each representation of the plurality of representations of protein building blocks within the representation of the symmetric protein architecture can include computationally aligning the symmetry axis of the representation of the protein building block with at least one axis of the representation of the symmetric protein architecture. In particular embodiments, determining the representation of the docked configuration of the symmetric protein architecture can include: after computationally aligning the symmetry axis of each representation of the plurality of representations of protein building blocks with at least one axis of the representation of the symmetric protein architecture, sampling a rotational degree of freedom and a translational degree of freedom of the representation of the symmetric protein architecture.

In more particular embodiments, sampling the rotational degree of freedom and the translational degree of freedom of the representation of the symmetric protein architecture can include: selecting a rotational value for the rotational degree of freedom; selecting a translational value for the translational degree of freedom; determining a representation of the symmetric protein architecture based on the rotational value and the translational value; determining a designability measure for the representation of the symmetric protein architecture, wherein the designability measure comprises a measure of suitability of the symmetric protein architecture for design; and generating a designability heat map based on the rotational value, translational value, and designability measure. In even more particular embodiments, determining the designability measure of the representation of the symmetric protein architecture can include determining a number of beta carbon contacts within a specified distance threshold between the plurality of representations of protein building blocks in the symmetric protein architecture based on the rotational value and the translational value. In other more particular embodiments, determining the designability measure of the representation of the symmetric protein architecture can include determining the energy of the contacts between neighboring protein building blocks using a computational score function. In still other more particular embodiments, determining the designability measure of the representation of the symmetric protein architecture can include determining an area of contact between at least two protein building blocks of the plurality of protein building blocks.

In other embodiments, the docked configuration of the symmetric protein architecture can include a cage-like or shell-like structure. In some embodiments, the cage-like or shell-like structure can enclose one or more molecules. In particular embodiments, the one or more enclosed molecules can be unrelated to the protein nanomaterial. In other embodiments, the cage-like or shell-like structure can display one or more molecules on a surface of the cage-like or shell-like structure. In other particular embodiments, the one or more molecules displayed on the surface can be unrelated to the protein nanomaterial.

At block 130, the computing device can computationally modify an amino acid sequence of docked protein building blocks to specify representations of protein-protein interfaces between the plurality of protein building blocks that are energetically favorable to drive self-assembly of a protein comprising the modified amino acid sequence to the docked configuration.

In some embodiments, computationally modifying the amino acid sequence of the docked protein building blocks to specify the protein-protein interfaces between the plurality of protein building blocks that are energetically favorable to drive self-assembly of the protein can include determining a representation of one or more amino acid sequences associated with a representation of at least one protein building block of the plurality of protein building blocks. In particular embodiments, computationally modifying the amino acid sequence of the docked protein building blocks to specify the protein-protein interfaces between the plurality of protein building blocks that are energetically favorable to drive self-assembly of the protein can include mutating an amino acid sequence for a selected representation of the one or more amino acid sequences.

In other embodiments, computationally modifying the amino acid sequence of the docked protein building blocks to specify the protein-protein interfaces between the plurality of protein building blocks that are energetically favorable to drive self-assembly of the protein can include evaluating an energy of an amino acid mutation using a computational score function.

At block 140, the computing device can generate an output based on at least one representation of the group consisting of the representation of the docked configuration of the symmetric protein architecture, the representations of protein-protein interfaces between the plurality of protein building blocks that is energetically favorable to drive self-assembly of a protein, and a representation of the protein comprising the modified amino acid sequence to the docked configuration.

Polypeptides

In a further aspect, the present invention provides isolated polypeptides comprising or consisting of the amino acid sequence of SEQ ID NO:1, wherein any defined residue in SEQ ID NO:1 can be modified by a conservative amino acid substitution, and wherein the polypeptide does not comprise or consist of the amino acid sequence of SEQ ID NO: 7 (wild type 3n79).

A polypeptide according to this aspect of the invention is capable of self-assembly with identical polypeptides to form multimers (i.e., dimers, trimers, tetramers, pentamers, octamers, etc.) The polypeptides of the invention are representative polypeptides that can be designed according to the computational methods of the invention; specifics of the design of the polypeptides of the invention are provided in the examples that follow. As will be understood by those of skill in the art, the design methods of the invention can produce a wide variety of self-assembling polypeptides, and the methods are in no way limited to the design of the self-assembling polypeptides disclosed herein.

As used herein, a "defined residue" means an amino acid position in the sequence listing that recites a specific amino acid residue. All undefined residues in SEQ ID NO:1 (i.e., residues that do not include a defined residue) are present on the polypeptide surface, and thus can be substituted with a different amino acid as desired for a given purpose without disruption of the polypeptide structure that permits polypeptide self-assembly. All defined residues are present in the polypeptide interior, and thus can be modified only by conservative substitutions to maintain overall polypeptide structure to permit polypeptide self-assembly. As used here, "conservative amino acid substitution" means that:
- hydrophobic amino acids (Ala, Cys, Gly, Pro, Met, Sce, Sme, Val, Ile, Leu) can only be substituted with other hydrophobic amino acids;
- hydrophobic amino acids with bulky side chains (Phe, Tyr, Trp) can only be substituted with other hydrophobic amino acids with bulky side chains;
- amino acids with positively charged side chains (Arg, His, Lys) can only be substituted with other amino acids with positively charged side chains;
- amino acids with negatively charged side chains (Asp, Glu) can only be substituted with other amino acids with negatively charged side chains; and
- amino acids with polar uncharged side chains (Ser, Thr, Asn, Gln) can only be substituted with other amino acids with polar uncharged side chains.

For ease of review, Table 1 provides a representation of SEQ ID NO:1, where the term "AA-" refers to the amino acid residue within SEQ ID NO:1, and the term "any" means an undefined residue. As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

TABLE 1

| | | | |
|---|---|---|---|
| AA1 | M | AA2 | ANY |
| AA3 | ANY | AA4 | A |
| AA5 | I | AA6 | G |
| AA7 | I | AA8 | L |
| AA9 | E | AA9 | L |
| AA11 | ANY | AA12 | S |
| AA13 | I | AA14 | A |
| AA15 | A | AA16 | G |
| AA17 | M | AA18 | E |
| AA19 | L | AA20 | G |
| AA21 | D | AA22 | A |
| AA23 | M | AA24 | L |
| AA25 | ANY | AA26 | S |
| AA27 | A | AA28 | ANY |
| AA29 | V | AA30 | ANY |
| AA31 | L | AA32 | L |
| AA33 | V | AA34 | S |
| AA35 | ANY | AA36 | T |
| AA37 | I | AA38 | ANY |
| AA39 | ANY | AA40 | G |
| AA41 | ANY | AA42 | F |
| AA43 | L | AA44 | L |
| AA45 | M | AA46 | L |
| AA47 | G | AA48 | G |
| AA49 | ANY | AA50 | ANY |
| AA51 | G | AA52 | A |
| AA53 | I | AA54 | Q |
| AA55 | ANY | AA56 | A |
| AA57 | I | AA58 | E |
| AA59 | T | AA60 | G |
| AA61 | T | AA62 | S |
| AA63 | Q | AA64 | A |
| AA65 | G | AA66 | E |
| AA67 | L | AA68 | ANY |
| AA69 | ANY | AA70 | ANY |
| AA71 | S | AA72 | ANY |
| AA73 | V | AA74 | L |
| AA75 | ANY | AA76 | ANY |
| AA77 | I | AA78 | ANY |
| AA79 | ANY | AA80 | S |
| AA81 | V | AA82 | L |
| AA83 | ANY | AA84 | A |
| AA85 | I | AA86 | ANY |
| AA87 | ANY | AA88 | ANY |
| AA89 | N | AA90 | ANY |
| AA91 | V | AA92 | ANY |
| AA93 | ANY | AA94 | ANY |
| AA95 | ANY | AA96 | A |
| AA97 | V | AA98 | G |
| AA99 | I | AA100 | V |
| AA101 | E | AA102 | T |
| AA103 | ANY | AA104 | S |
| AA105 | V | AA106 | A |
| AA107 | A | AA108 | C |
| AA109 | I | AA110 | S |
| AA111 | A | AA112 | A |
| AA113 | D | AA114 | ANY |
| AA115 | A | AA116 | V |
| AA117 | ANY | AA118 | G |
| AA119 | S | AA120 | ANY |
| AA121 | V | AA122 | T |

TABLE 1-continued

| | | | |
|---|---|---|---|
| AA123 | L | AA124 | V |
| AA125 | R | AA126 | V |
| AA127 | ANY | AA128 | M |
| AA129 | A | AA130 | ANY |
| AA131 | G | AA132 | I |
| AA133 | ANY | AA134 | G |
| AA135 | K | AA136 | C |
| AA137 | Y | AA138 | M |
| AA139 | V | AA140 | V |
| AA141 | A | AA142 | G |
| AA143 | ANY | AA144 | V |
| AA145 | S | AA146 | D |
| AA147 | V | AA148 | A |
| AA149 | L | AA150 | A |
| AA151 | V | AA152 | T |
| AA153 | V | AA154 | A |
| AA155 | S | AA156 | S |
| AA157 | S | AA158 | A |
| AA159 | G | AA160 | A |
| AA161 | Y | AA162 | ANY |
| AA163 | L | AA164 | L |
| AA165 | V | AA166 | Y |
| AA167 | A | AA168 | S |
| AA169 | L | AA170 | I |
| AA171 | ANY | AA172 | ANY |
| AA173 | P | AA174 | ANY |
| AA175 | ANY | AA176 | A |
| AA177 | M | AA178 | ANY |
| AA179 | ANY | AA180 | Q |
| AA181 | M | AA182 | V |
| AA183 | ANY | AA184 | ANY |

In one embodiment, a polypeptide of this aspect of the invention includes at least 2, 3, 4, 5, 6, 7, 8, 9, 10, or more amino acid substitutions relative to SEQ ID NO: 7. In one such embodiment, at least two of the following amino acid positions are changed relative to SEQ ID NO:7: AA14, AA67, AA148, AA149, AA156, AA160, AA161, AA167, and AA 169. In various embodiments, 2, 3, 4, 5, 6, 7, 8, or all 9 residues (AA14, AA67, AA148, AA149, AA156, AA160, AA161, AA167, and AA 169) in the polypeptides of this aspect of the invention are changed relative to SEQ ID NO:7.

In a further embodiment, the polypeptides of this aspect of the invention include no more than 100 defined residues as per SEQ ID NO:1 are modified by a conservative amino acid substitution. In various further embodiments, no more than 90, 85, 80, 75, 70, 65, 60, 55, 50, 45, 40, 35, 30, 25, 30, 15, 10, 9, 8, 7, 6, 5, 4, 3, 2, or 1 defined residues as per SEQ ID NO:1 are modified by a conservative amino acid substitution. In a further embodiment, the polypeptide comprise or consist of SEQ ID NO:1 with no defined residues modified by a conservative amino acid substitution.

In a further embodiment, a polypeptide of this aspect of the invention comprises or consists of an amino acid sequence with at least 75% identity to the amino acid sequence of SEQ ID NO:2 (also referred to herein as "O3-33"). In various embodiments, the polypeptide comprises or consists of an amino acid sequence with at least 80%, 85%, 90%, 95%, 96%, 97%, 98%, or 99% identity to the amino acid sequence of SEQ ID NO:2. In each of these embodiments, it is understood that residues in SEQ ID NO:2 corresponding to defined residues in SEQ ID NO:1 may only be substituted by conservative amino acid substitutions. In another embodiment, a polypeptide of the second aspect of the invention comprises or consists of the amino acid sequence of SEQ ID NO:2 (O3-33), which is discussed by way of example herein.

In a further aspect, the present invention provides isolated polypeptides comprising or consisting of the amino acid sequence of SEQ ID NO:3, wherein any defined residue in SEQ ID NO:3 can be modified by a conservative amino acid substitution, and wherein the polypeptide does not comprise or consist of the amino acid sequence of SEQ ID NO: 8 (3 ftt-wt).

A polypeptide according to this aspect of the invention is also capable of self-assembly with identical polypeptides to form multimers (i.e., dimers, trimers, tetramers, pentamers, octamers, etc.) The polypeptides of this aspect of the invention are also representative polypeptides that can be designed according to the computational methods of the invention; specifics of the design of the polypeptides of the invention are provided in the examples that follow. All definitions provided herein apply equally to this third aspect of the invention.

For ease of review, Table 2 provides a representation of SEQ ID NO:3, where the term "AA-" refers to the amino acid residue within SEQ ID NO:3, and the term "any" means an undefined residue.

TABLE 2

| | | | |
|---|---|---|---|
| AA1 | M | AA2 | ANY |
| AA3 | ANY | AA4 | ANY |
| AA5 | ANY | AA6 | ANY |
| AA7 | ANY | AA8 | ANY |
| AA9 | ANY | AA9 | ANY |
| AA11 | K | AA12 | W |
| AA13 | ANY | AA14 | D |
| AA15 | A | AA16 | ANY |
| AA17 | F | AA18 | D |
| AA19 | ANY | AA20 | T |
| AA21 | ANY | AA22 | I |
| AA23 | N | AA24 | E |
| AA25 | R | AA26 | L |
| AA27 | R | AA28 | A |
| AA29 | K | AA30 | V |
| AA31 | I | AA32 | C |
| AA33 | F | AA34 | A |
| AA35 | L | AA36 | N |
| AA37 | H | AA38 | T |
| AA39 | N | AA40 | P |
| AA41 | S, V | AA42 | ANY |
| AA43 | T | AA44 | L, M |
| AA45 | K, M | AA46 | ANY |
| AA47 | K | AA48 | V |
| AA49 | L | AA50 | I |
| AA51 | D | AA52 | A |
| AA53 | L | AA54 | F |
| AA55 | Q | AA56 | T |
| AA57 | T | AA58 | ANY |
| AA59 | ANY | AA60 | N |
| AA61 | ANY | AA62 | S |
| AA63 | I | AA64 | S |
| AA65 | I | AA66 | P |
| AA67 | F | AA68 | D |
| AA69 | T | AA70 | D |
| AA71 | Y | AA72 | G |
| AA73 | W | AA74 | N |
| AA75 | ANY | AA76 | K |
| AA77 | L | AA78 | ANY |
| AA79 | ANY | AA80 | N |
| AA81 | V | AA82 | Y |
| AA83 | V | AA84 | N |
| AA85 | T | AA86 | N |
| AA87 | C | AA88 | Y |
| AA89 | F | AA90 | M |
| AA91 | D | AA92 | ANY |
| AA93 | G | AA94 | ANY |
| AA95 | I | AA96 | T |
| AA97 | ANY | AA98 | G |
| AA99 | D | AA100 | N |
| AA101 | V | AA102 | F |
| AA103 | I | AA104 | G |
| AA105 | P | AA106 | N |
| AA107 | C | AA108 | G |
| AA109 | F | AA110 | Y |
| AA111 | ANY | AA112 | A |
| AA113 | T | AA114 | ANY |
| AA115 | P | AA116 | ANY |
| AA117 | ANY | AA118 | ANY |

TABLE 2-continued

| | | | |
|---|---|---|---|
| AA119 | H | AA120 | H |
| AA121 | ANY | AA122 | N |
| AA123 | ANY | AA124 | G |
| AA125 | ANY | AA126 | E |
| AA127 | K | AA128 | A |
| AA129 | G | AA130 | ANY |
| AA131 | I | AA132 | H |
| AA133 | I | AA134 | G |
| AA135 | S | AA136 | N |
| AA137 | T | AA138 | W |
| AA139 | F | AA140 | G |
| AA141 | G | AA142 | H |
| AA143 | V | AA144 | A |
| AA145 | V | AA146 | L |
| AA147 | P | AA148 | ANY |
| AA149 | V | AA150 | T |
| AA151 | ANY | AA152 | G |
| AA153 | E | AA154 | G |
| AA155 | S | AA156 | V |
| AA157 | I | AA158 | G |
| AA159 | A | AA160 | G |
| AA161 | S | AA162 | V |
| AA163 | ANY | AA164 | ANY |
| AA165 | K | AA166 | ANY |
| AA167 | ANY | AA168 | ANY |
| AA169 | P | AA170 | H |
| AA171 | S | AA172 | ANY |
| AA173 | A | AA174 | V |
| AA175 | ANY | AA176 | N |
| AA177 | ANY | AA178 | ANY |
| AA179 | ANY | AA180 | ANY |
| AA181 | ANY | AA182 | R |
| AA183 | ANY | AA184 | I |
| AA185 | ANY | AA186 | ANY |
| AA187 | D | AA188 | L |
| AA189 | P | AA190 | S |
| AA191 | E | AA192 | T |
| AA193 | L | AA194 | N |
| AA195 | D | AA196 | E |
| AA197 | T | AA198 | I |
| AA199 | K | | |

In one embodiment, a polypeptide of this aspect of the invention includes at least 2, 3, 4, 5, 6, 7, 8, 9, 10, or more amino acid substitutions relative to SEQ ID NO: 8. In one such embodiment, at least two of the following amino acid positions are changed relative to SEQ ID NO:8: AA20, AA26, AA30, AA34, AA39, AA41, AA44, AA48, and AA 52. In various embodiments, 2, 3, 4, 5, 6, 7, 8, or all 9 residues (AA20, AA26, AA30, AA34, AA39, AA41, AA44, AA48, and AA 52) in the polypeptides of the second aspect of the invention are changed relative to SEQ ID NO:8.

In a further embodiment, the polypeptides of this aspect of the invention include no more than 100 defined residues as per SEQ ID NO:3 are modified by a conservative amino acid substitution. In various further embodiments, no more than 90, 85, 80, 75, 70, 65, 60, 55, 50, 45, 40, 35, 30, 25, 30, 15, 10, 9, 8, 7, 6, 5, 4, 3, 2, or 1 defined residues as per SEQ ID NO:3 are modified by a conservative amino acid substitution. In a further embodiment, the polypeptide comprise or consist of SEQ ID NO:3 with no defined residues modified by a conservative amino acid substitution.

In a further embodiment, a polypeptide of this aspect of the invention comprises or consists of an amino acid sequence with at least 75% identity to an amino acid sequence selected from the group consisting of SEQ ID NO:4, SEQ ID NO:5 (also referred to herein as "T3-08"), and SEQ ID NO:6 (also referred to herein as "T3-10"). In various embodiments, the polypeptide comprises or consists of an amino acid sequence with at least 80%, 85%, 90%, 95%, 96%, 97%, 98%, or 99% identity to an amino acid sequence selected from the group consisting of SEQ ID NO:4, SEQ ID NO:5, and SEQ ID NO:6. In each of these embodiments, it is understood that residues in SEQ ID NO:4, 5, or 6 corresponding to defined residues in SEQ ID NO:3 may only be substituted by conservative amino acid substitutions. In another embodiment, a polypeptide of this aspect of the invention comprises or consists of an amino acid sequence selected from the group consisting of SEQ ID NO:4, SEQ ID NO:5, and SEQ ID NO:6, which are discussed by way of example herein.

As will be apparent to those of skill in the art, the ability to widely modify surface amino acid residues without disruption of the polypeptide structure permits many types of modifications to endow the resulting self-assembled polypeptides with a variety of functions. In one non-limiting embodiment, the polypeptides can be modified to facilitate covalent linkage to a "cargo" of interest. In one non-limiting example, the polypeptide can be modified, such as by introduction of various cysteine residues at defined positions to facilitate linkage to one or more antigens of interest, such that an assembly of the polypeptides would provide a scaffold to provide a large number of antigens for delivery as a vaccine to generate an improved immune response (similar to the use of virus-like particles). In another non-limiting embodiment, the polypeptides of the invention may be modified by linkage (covalent or non-covalent) with a moiety to help facilitate "endosomal escape." For applications that involve delivering molecules of interest to a target cell, such as targeted delivery, a critical step can be escape from the endosome—a membrane-bound organelle that is the entry point of the delivery vehicle into the cell. Endosomes mature into lysosomes, which degrade their contents. Thus, if the delivery vehicle does not somehow "escape" from the endosome before it becomes a lysosome, it will be degraded and will not perform its function. There are a variety of lipids or organic polymers that disrupt the endosome and allow escape into the cytosol. Thus, in this embodiment, the polypeptide monomer can be modified, for example, by introducing cysteine residues that will allow chemical conjugation of such a lipid or organic polymer to the monomer or resulting multimer surface.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to any other moiety as deemed useful for a given purpose. Such linkage can be covalent or non-covalent as is understood by those of skill in the art.

In a further aspect, the present invention provides multimers, comprising a plurality of identical polypeptide monomers according to any embodiment or combination of embodiments of the polypeptides of the invention. As is disclosed herein, polypeptides of the invention are capable of self-assembling into multimeric assemblies (i.e.: dimers, trimers, hexamers, pentamers, octamers, etc.) formed from self-assembly of a plurality of a single polypeptide monomer of the invention (i.e., "homo-multimeric assemblies"). As used herein, a "plurality" means 2 or more. In various embodiments, the multimeric assembly comprises 3, 4, 5, 6, 7, 8, 9, 10, 11, 12, or more identical polypeptide monomers. The multimeric assemblies can be used for any purpose, and provide a way to develop a wide array of protein "nanomaterials." In addition to the finite, cage-like or shell-like protein assemblies described in the examples, unbounded materials in one, two, or three dimensions (i.e., fibers/helices, layers, or crystals) may be designed by choosing an appropriate target symmetric architecture. The monomers and/or multimeric assemblies of the invention can be used in the design of higher order assemblies with the attendant advantages of hierarchical assembly. The resulting multimeric assemblies are highly ordered materials with superior rigidity and monodispersity, and can form the basis of advanced functional materials and custom-designed molecular machines with wide-ranging applications.

In another aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a further aspect, the present invention provides recombinant expression vectors comprising the isolated nucleic acid of any embodiment or combination of embodiments of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide.

Computational Methods for Designing Self-Assembled Polypeptides

As indicated above, a general computational method for designing self-assembling protein materials can involve two techniques: 1) symmetrical docking of protein building blocks in a target symmetric architecture followed by 2) design of low energy protein-protein interfaces between the building blocks to drive self-assembly.

Figure 2A:
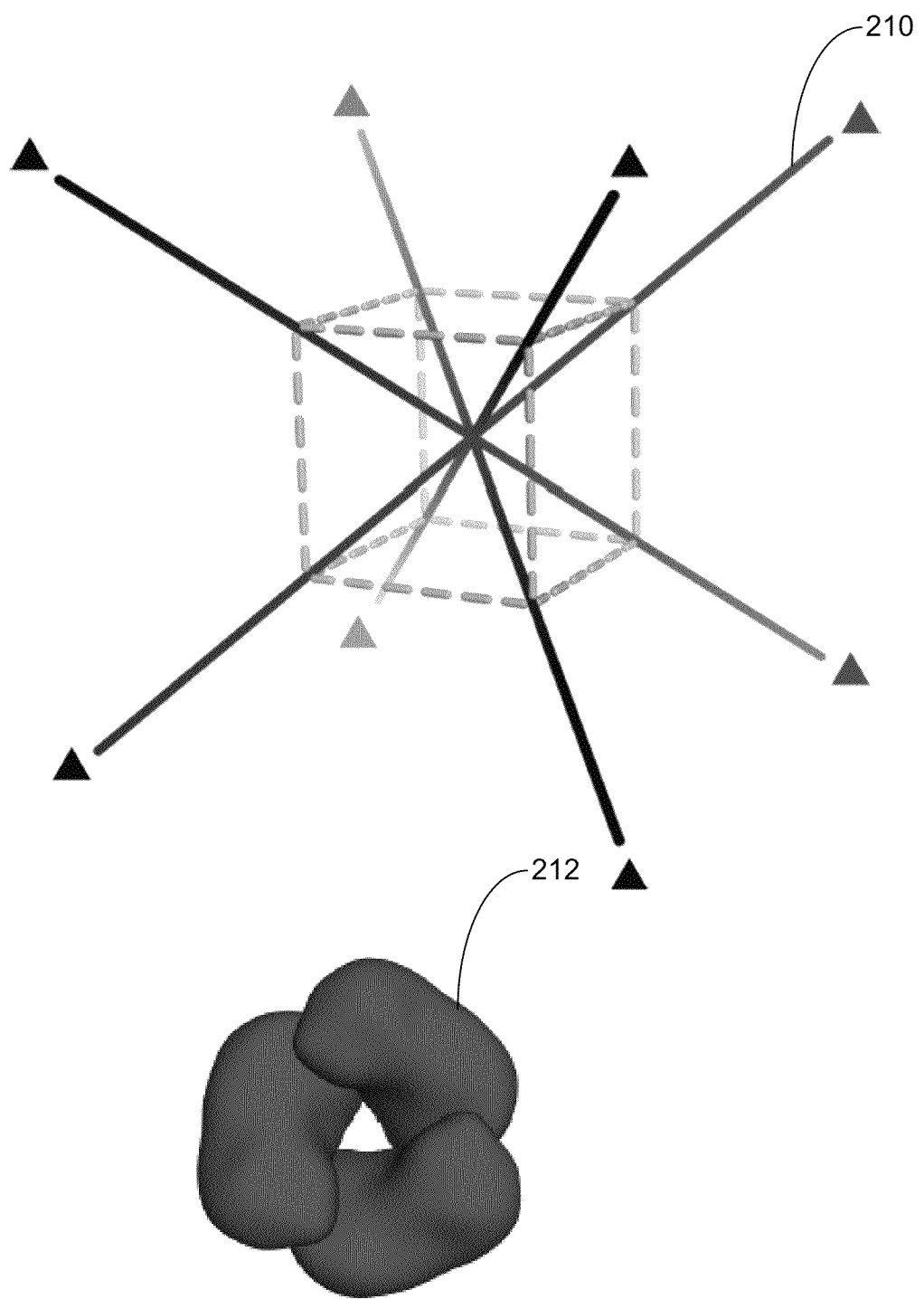
FIG. 2A shows an example target architecture for designing self-assembled polypeptides and an example protein building block

In one general approach to designing self-assembling protein nanomaterials, a target symmetric architecture is chosen. FIG. 2A shows an example target architecture 210 having octahedral point group symmetry, with three-fold rotational axes marked with triangles and shown in with black lines. In other examples, target architectures can be used that conform to a symmetry such as, but not limited to, a cyclic point group symmetry, a dihedral point group symmetry, a cubic point group symmetry, a line group symmetry, a plane group symmetry, a layer group symmetry, and a space group symmetry.

In certain embodiments of the present disclosure libraries or other sources of information regarding protein of various structures and symmetries can be used to select candidates for protein building blocks. FIG. 2A shows a C3 symmetric trimer 220 an example candidate protein building block.

In some cases, a protein building block, such as trimer 220, can share a degree of symmetry with target architecture 210. Then, the number of new protein-protein interfaces to be designed is reduced by one, since the interface within an oligomer protein building block contributes to the self-assembly of the subunits to the target material. Furthermore, the energetic contribution of each designed interaction is multiplied by the symmetry of the building block, which reduces the number of distinct new interactions used to overcome the entropic cost of self-assembly.

A set of trimeric proteins used as input structures to a design protocol was obtained by first searching the PISA database for homotrimeric proteins with an average chain length of less than 200 amino acids. This list was cross-referenced against the results of a search of the 3D Complex database for homotrimeric proteins with C3 symmetry and the intersection of the two lists was then clustered at 95% sequence identity to identify a representative structure from each cluster. The final list included the 271 proteins identified by PDB ID below. Many of the proteins in the list were judged visually during the design process to not be trimeric.

Coordinates for each of the 271 proteins were downloaded from the Protein Data Bank (http://www.rcsb.org/pdb/), the trimeric axis was aligned along the vector [0,0,1], and the center of mass of the trimer translated to the origin. A single subunit of each trimer was used as input into our design protocol without further modification.

A resulting example trimeric scaffold protein set included the following structures listed in Table 3 below.

TABLE 3

|  | 1a3f | 1a8m | 1aa0 | 1afa | 1ahs | 1aly | 1ax8 | 1b4b | 1baw | 1ble |
|---|---|---|---|---|---|---|---|---|---|---|
| 1c5e | 1ca4 | 1dbf | 1dg6 | 1di7 | 1dpt | 1duc | 1dxc | 1e20 | 1env | 1eq7 |
| 1f3g | 1f7l | 1f7r | 1gnk | 1gr3 | 1h7z | 1h9j | 1hfo | 1htn | 1hup | 1iby |
| 1ihc | 1ij0 | 1ij1 | 1iv1 | 1jpx | 1jq0 | 1js0 | 1k33 | 1kd7 | 1kfn | 1knb |
| 1kqa | 1kr4 | 1l1s | 1lr0 | 1mff | 1mof | 1nig | 1nob | 1nog | 1nq3 | 1nza |
| 1o5l | 1o8n | 1o9l | 1ocy | 1oni | 1otg | 1ox3 | 1p1l | 1p4t | 1p9h | 1pf5 |
| 1pil | 1piq | 1q0p | 1q3i | 1q89 | 1qah | 1qd9 | 1qhv | 1qu9 | 1qzu | 1r13 |
| 1rhy | 1rlh | 1rnj | 1s55 | 1s9z | 1t0a | 1t2n | 1td3 | 1tul | 1u9d | 1ufy |
| 1ug4 | 1uiz | 1uku | 1usn | 1uwn | 1v3w | 1vbv | 1vck | 1ve0 | 1vi4 | 1vmh |
| 1w16 | 1wdf | 1wfx | 1woz | 1wyy | 1x25 | 1x90 | 1xhd | 1xho | 1ygs | 1yq8 |
| 1yvs | 1z8k | 1zvc | 1zvq | 2b33 | 2baz | 2bs5 | 2bsf | 2bzu | 2cgy | 2cmp |
| 2csl | 2cwj | 2d4l | 2d4z | 2dt4 | 2ebo | 2ed6 | 2eg1 | 2f7w | 2fb6 | 2fkk |
| 2flz | 2fvh | 2g2c | 2g2d | 2gw8 | 2h3m | 2h6l | 2h8a | 2hew | 2hx0 | 2ic7 |
| 2j97 | 2j9c | 2jbz | 2nuh | 2ose | 2ot5 | 2otm | 2p23 | 2p4v | 2p6c | 2p6h |
| 2p6y | 2pd2 | 2pmp | 2pno | 2pnv | 2q5u | 2qe3 | 2qg8 | 2qgr | 2qih | 2r32 |
| 2r6q | 2re9 | 2rfr | 2rhd | 2tnf | 2ux6 | 2v18 | 2vhe | 2vky | 2w6b | 2w9n |
| 2wb3 | 2wh7 | 2wl7 | 2wpq | 2wps | 2wpy | 2wq1 | 2wst | 2ww6 | 2ww7 | 2wz7 |
| 2x29 | 2x4j | 2xbp | 2xcd | 2xcz | 2xdh | 2xmw | 2yw4 | 2yzj | 2zfc | 3b6n |
| 3b8l | 3bq4 | 3bzq | 3c19 | 3ce8 | 3ci1 | 3ck2 | 3cnc | 3cp1 | 3d8m | 3de9 |
| 3dww | 3e6q | 3eby | 3efg | 3ejc | 3ejv | 3elo | 3emo | 3esj | 3exv | 3exw |
| 3f6m | 3f91 | 3fk3 | 3ftt | 3fwt | 3fwu | 3gmj | 3gtz | 3gud | 3gwm | 3h5i |
| 3h7z | 3h88 | 3h9n | 3hhl | 3hon | 3hro | 3hwu | 3hza | 3i7t | 3i9f | 3i9z |
| 3ipz | 3irc | 3is8 | 3ivl | 3ixc | 3jsc | 3jv1 | 3k9a | 3kjj | 3kwd | 3kxr |
| 3l8r | 3laa | 3lqw | 3m06 | 3m1x | 3mc3 | 3md1 | 3mdx | 3mgw | 3mh5 | 3mpv |
| 3mxu | 3n3f | 3n79 | 3nbt | 3ne1 | 3nv1 | 3o46 | 3oi9 |  |  |  |

In certain embodiments of the present disclosure the symmetry of the oligomeric protein building blocks can be modeled. A general framework for modeling arbitrary symmetric systems has been implemented in Rosetta. In some embodiments, this framework can be used to dock subunits of protein trimers in configurations with octahedral and tetrahedral symmetry while maintaining the relative orientation of the subunits within the trimer, such as docked configuration 230.

However, other methods and software systems could be used to model the symmetry of the oligomeric protein building blocks. The symmetry of the target architecture, such as target architecture 210, can be passed to Rosetta in the form of a symmetry definition file. The symmetry definition files used in this study to model octahedra and tetrahedra constructed from trimers ("O3" and "T3" complexes) include Rosetta instructions shown in Table 4 below.

TABLE 4 symmetry_name O3
subunits 24
number_of_interfaces 23
E =
2 * B1_1 + B1_1:B1_2 + B1_1:B1_3 + B1_1:B2_1 + B1_1:B2_2 + B1_1:B2_3 + B1_1:B3_1 + B1_1:B3_2 + B1_1:B3_3 + B1_1:B4_1 + B1_1:B4_2 + B1_1:B4_3 + B1_1:B5_1 + B1_1:B5_2 + B1_1:B5_3 + B1_1:B6_1 + B1_1:B6_2 + B1_1:B6_3 + B1_1:B7_1 + B1_1:B7_2 + B1_1:B7_3 + B1_1:B8_1 + B1_1:B8_2 + B1_1:B8_3
anchor_residue COM
virtual_coordinates_start
xyz C1 0.000000000000000, 0.000000000000000, 1.000000000000000
1.000000000000000, −0.000000000000000, 0.000000000000000 0, 0, 0
xyz P1 0.000000000000000, 0.000000000000000, 1.000000000000000
1.000000000000000, −0.000000000000000, 0.000000000000000 0, 0, 0
xyz B1_1 0.000000000000000, 0.000000000000000, 1.000000000000000
1.000000000000000, −0.000000000000000, 0.000000000000000 0, 0, 0
xyz B1_2 0.000000000000000, 0.000000000000000, 1.000000000000000
0.500000000000000, 0.866025403784439, 0.000000000000000 0, 0, 0
xyz B1_3 0.000000000000000, 0.000000000000000, 1.000000000000000
0.500000000000001, −0.866025403784438, 0.000000000000000 0, 0, 0
xyz C2 0.666666666666667, 0.666666666666667, 0.333333333333333
0.666666666666667, −0.333333333333333, −0.666666666666667 0, 0, 0
xyz P2 0.666666666666667, 0.666666666666667, 0.333333333333333
0.666666666666667, −0.333333333333333, −0.666666666666667 0, 0, 0
xyz B2_1 0.666666666666667, 0.666666666666667, 0.333333333333333
0.666666666666667, −0.333333333333333, −0.666666666666667 0, 0, 0
xyz B2_2 0.666666666666667, 0.666666666666667, 0.333333333333333
0.044658198738520, −0.410683602522959, 0.910683602522959 0, 0, 0
xyz B2_3 0.666666666666667, 0.666666666666667, 0.333333333333333
0.622008467928146, 0.744016935856292, −0.244016935856292 0, 0, 0
xyz C3 0.244016935856292, −0.910683602522959, 0.333333333333333
0.955341801261480, 0.166666666666667, −0.244016935856292 0, 0, 0
xyz P3 0.244016935856292, −0.910683602522959, 0.333333333333333
0.955341801261480, 0.166666666666667, −0.244016935856292 0, 0, 0
xyz B3_1 0.244016935856292, −0.910683602522959, 0.333333333333333
0.955341801261480, 0.166666666666667, −0.244016935856292 0, 0, 0

TABLE 4-continued

```
xyz B3__2 0.244016935856292, −0.910683602522959, 0.333333333333333
0.622008467928146, −0.410683602522959, −0.666666666666667 0, 0, 0
xyz B3__3 0.244016935856292, −0.910683602522959, 0.333333333333333
−0.333333333333334, 0.244016935856292, 0.910683602522959 0, 0, 0
xyz C4 0.910683602522959, −0.244016935856292, −0.333333333333333
0.244016935856292, 0.333333333333333, −0.910683602522959 0, 0, 0
xyz P4 0.910683602522959, −0.244016935856292, −0.333333333333333
0.244016935856292, 0.333333333333333, −0.910683602522959 0, 0, 0
xyz B4__1 0.910683602522959, −0.244016935856292, −0.333333333333333
−0.244016935856292, 0.333333333333333, −0.910683602522959 0, 0, 0
xyz B4__2 0.910683602522959, −0.244016935856292, −0.333333333333333
−0.166666666666667, −0.955341801261480, 0.244016935856292 0, 0, 0
xyz B4__3 0.910683602522959, −0.244016935856292, −0.333333333333333
0.410683602522959, 0.622008467928146, 0.666666666666667 0, 0, 0
xyz C5 −0.910683602522959, 0.244016935856292, 0.333333333333333
0.377991532071854, 0.166666666666667, 0.910683602522959 0, 0, 0
xyz P5 −0.910683602522959, 0.244016935856292, 0.333333333333333
0.377991532071854, 0.166666666666667, 0.910683602522959 0, 0, 0
xyz B5__1 −0.910683602522959, 0.244016935856292, 0.333333333333333
0.377991532071854, 0.166666666666667, 0.910683602522959 0, 0, 0
xyz B5__2 −0.910683602522959, 0.244016935856292, 0.333333333333333
−0.333333333333333, −0.910683602522959, −0.244016935856292 0, 0, 0
xyz B5__3 −0.910683602522959, 0.244016935856292, 0.333333333333333
−0.044658198738521, 0.744016935856292, −0.666666666666667 0, 0, 0
xyz C6 −0.244016935856292, 0.910683602522959, −0.333333333333333
0.910683602522959, 0.333333333333333, 0.244016935856292 0, 0, 0
xyz P6 −0.244016935856292, 0.910683602522959, −0.333333333333333
0.910683602522959, 0.333333333333333, 0.244016935856292 0, 0, 0
xyz B6__1 −0.244016935856292, 0.910683602522959, −0.333333333333333
0.910683602522959, 0.333333333333333, 0.244016935856292 0, 0, 0
xyz B6__2 −0.244016935856292, 0.910683602522959, −0.333333333333333
−0.744016935856292, 0.044658198738520, 0.666666666666667 0, 0, 0
xyz B6__3 −0.244016935856292, 0.910683602522959, −0.333333333333333
−0.166666666666667, −0.377991532071854, −0.910683602522959 0, 0, 0
xyz C7 −0.666666666666667, −0.666666666666667, −0.333333333333333
0.333333333333333, −0.666666666666667, 0.666666666666667 0, 0, 0
xyz P7 −0.666666666666667, −0.666666666666667,
0.333333333333333, −0.333333333333333, −0.666666666666667,
0.666666666666667 0, 0, 0
xyz B7__1 −0.666666666666667, −0.666666666666667,,
0.333333333333333, 0.333333333333333, −0.666666666666667,
0.666666666666667 0, 0, 0
xyz B7__2 −0.666666666666667, −0.666666666666667,
0.333333333333333, −0.410683602522959, 0.044658198738520, −0.910683602522959
0, 0, 0
xyz B7__3 −0.666666666666667, −0.666666666666667,
0.333333333333333, −0.744016935856292, 0.622008467928146,
0.244016935856292 0, 0, 0
xyz C8 0.000000000000000, 0.000000000000000, 1.000000000000000,
0.000000000000000, −1.000000000000000, 0.000000000000000 0, 0, 0
xyz P8 0.000000000000000, 0.000000000000000, 1.000000000000000,
0.000000000000000, −1.000000000000000, 0.000000000000000 0, 0, 0
xyz B8__1 0.000000000000000, 0.000000000000000,
1.000000000000000, 0.000000000000000, −1.000000000000000,
0.000000000000000 0, 0, 0
xyz B8__2 0.000000000000000,
0.000000000000000, 1.000000000000000, 0.866025403784438, −0.500000000000000,
0.000000000000000 0, 0, 0
xyz B8__3 0.000000000000000, 0.000000000000000, 1.000000000000000
0.866025403784438, −0.500000000000001, −0.000000000000000 0, 0, 0
virtual_coordinates_stop
connect_virtual JP1 C1 P1
connect_virtual JP1__1 P1 B1__1
connect_virtual JB1__1 B1__1 SUBUNIT
connect_virtual JP1__2 P1 B1__2
connect_virtual JB1__2 B1__2 SUBUNIT
connect_virtual JP1__3 P1 B1__3
connect_virtual JB1__3 B1__3 SUBUNIT
connect_virtual JC2 C1 C2
connect_virtual JP2 C2 P2
connect_virtual JP2__1 P2 B2__1
connect_virtual JB2__1 B2__1 SUBUNIT
connect_virtual JP2__2 P2 B2__2
connect_virtual JB2__2 B2__2 SUBUNIT
connect_virtual JP2__3 P2 B2__3
connect_virtual JB2__3 B2__3 SUBUNIT
connect_virtual JC3 C1 C3
connect_virtual JP3 C3 P3
connect_virtual JP3__1 P3 B3__1
connect_virtual JB3__1 B3__1 SUBUNIT
```

TABLE 4-continued

```
connect_virtual JP3_2 P3 B3_2
connect_virtual JB3_2 B3_2 SUBUNIT
connect_virtual JP3_3 P3 B3_3
connect_virtual JB3_3 B3_3 SUBUNIT
connect_virtual JC4 C1 C4
connect_virtual JP4 C4 P4
connect_virtual JP4_1 P4 B4_1
connect_virtual JB4_1 B4_1 SUBUNIT
connect_virtual JP4_2 P4 B4_2
connect_virtual JB4_2 B4_2 SUBUNIT
connect_virtual JP4_3 P4 B4_3
connect_virtual JB4_3 B4_3 SUBUNIT
connect_virtual JC5 C1 C5
connect_virtual JP5 C5 P5
connect_virtual JP5_1 P5 B5_1
connect_virtual JB5_1 B5_1 SUBUNIT
connect_virtual JP5_2 P5 B5_2
connect_virtual JB5_2 B5_2 SUBUNIT
connect_virtual JP5_3 P5 B5_3
connect_virtual JB5_3 B5_3 SUBUNIT
connect_virtual JC6 C1 C6
connect_virtual JP6 C6 P6
connect_virtual JP6_1 P6 B6_1
connect_virtual JB6_1 B6_1 SUBUNIT
connect_virtual JP6_2 P6 B6_2
connect_virtual JB6_2 B6_2 SUBUNIT
connect_virtual JP6_3 P6 B6_3
connect_virtual JB6_3 B6_3 SUBUNIT
connect_virtual JC7 C1 C7
connect_virtual JP7 C7 P7
connect_virtual JP7_1 P7 B7_1
connect_virtual JB7_1 B7_1 SUBUNIT
connect_virtual JP7_2 P7 B7_2
connect_virtual JB7_2 B7_2 SUBUNIT
connect_virtual JP7_3 P7 B7_3
connect_virtual JB7_3 B7_3 SUBUNIT
connect_virtual JC8 C1 C8
connect_virtual JP8 C8 P8
connect_virtual JP8_1 P8 B8_1
connect_virtual JB8_1 B8_1 SUBUNIT
connect_virtual JP8_2 P8 B8_2
connect_virtual JB8_2 B8_2 SUBUNIT
connect_virtual JP8_3 P8 B8_3
connect_virtual JB8_3 B8_3 SUBUNIT
set_dof JP1 x angle_x
set_jump_group JGP JP1 JP2 JP3 JP4 JP5 JP6 JP7 JP8
set_jump_group JGB JB1_1 JB1_2 JB1_3 JB2_1 JB2_2 JB2_3 JB3_1
JB3_2 JB3_3 JB4_1 JB4_2 JB4_3 JB5_1 JB5_2 JB5_3 JB6_1 JB6_2
JB6_3 JB7_1 JB7_2 JB7_3 JB8_1 JB8_2 JB8_3
symmetry_name T3
subunits 12
number_of_interfaces 11
E =
2 * B1_1 + B1_1:B1_2 + B1_1:B1_3 + B1_1:B2_1 + B1_1:B2_2 + B1_1:B2_3 + B1_1:B3_1 +
B1_1:B3_2 + B1_1:B3_3 + B1_1:B4_1 + B1_1:B4_2 + B1_1:B4_3
anchor_residue COM
virtual_coordinates_start
xyz C1 0.000000000000000, 0.000000000000000, 1.000000000000000 −1.000000000000000,
−0.000000000000000, 0.000000000000000 0, 0, 0
xyz P1 0.000000000000000, 0.000000000000000, 1.000000000000000 −1.000000000000000,
−0.000000000000000, 0.000000000000000 0, 0, 0
xyz B1_1 0.000000000000000, 0.000000000000000, 1.000000000000000 −1.000000000000000,
−0.000000000000000, 0.000000000000000 0, 0, 0
xyz B1_2 0.000000000000000, 0.000000000000000, 1.000000000000000
0.500000000000000, 0.866025403784439, 0.000000000000000 0, 0, 0
xyz B1_3 0.000000000000000, 0.000000000000000, 1.000000000000000
0.500000000000001, −0.866025403784438, 0.000000000000000 0, 0, 0
xyz C2 −0.666666666666667, −0.666666666666667, −0.333333333333333
0.333333333333333, −0.666666666666667, 0.666666666666667 0, 0, 0
xyz P2 −0.666666666666667, −0.666666666666667, −0.333333333333333
0.333333333333333, −0.666666666666667, 0.666666666666667 0, 0, 0
xyz B2_1 −0.666666666666667, −0.666666666666667, −0.333333333333333
0.333333333333333, −0.666666666666667,
0.666666666666667 0, 0, 0
xyz B2_2 −0.666666666666667, −0.666666666666667, −0.333333333333333
0.410683602522959, 0.044658198738520, −0.910683602522959
0, 0, 0
xyz B2_3 −0.666666666666667, −0.666666666666667, −0.333333333333333
−0.744016935856292,
```

TABLE 4-continued

```
0.622008467928146, 0.244016935856292 0, 0, 0
xyz C3 −0.244016935856292, 0.910683602522959, −0.333333333333333
0.910683602522959, 0.333333333333333, 0.244016935856292 0, 0, 0
xyz P3 −0.244016935856292, 0.910683602522959, −0.333333333333333
0.910683602522959, 0.333333333333333, 0.244016935856292 0, 0, 0
xyz B3__1 −0.244016935856292, 0.910683602522959, −0.333333333333333
0.910683602522959, 0.333333333333333, 0.244016935856292 0, 0, 0
xyz B3__2 −0.244016935856292, 0.910683602522959, −0.333333333333333
−0.744016935856292, 0.044658198738520, 0.666666666666667 0, 0, 0
xyz B3__3 −0.244016935856292, 0.910683602522959, −0.333333333333333
−0.166666666666667, −0.377991532071854, −0.910683602522959 0, 0, 0
xyz C4 0.910683602522959, −0.244016935856292, −0.333333333333333 −0.244016935856292,
0.333333333333333, −0.910683602522959 0, 0, 0
xyz P4 0.910683602522959, −0.244016935856292, −0.333333333333333 −0.244016935856292,
0.333333333333333, −0.910683602522959 0, 0, 0
xyz B4__1 0.910683602522959, −0.244016935856292, −0.333333333333333
−0.244016935856292, 0.333333333333333, −0.910683602522959 0, 0, 0
xyz B4__2 0.910683602522959, −0.244016935856292, −0.333333333333333
−0.166666666666667, −0.955341801261480, 0.244016935856292 0, 0, 0
xyz B4__3 0.910683602522959, −0.244016935856292, −0.333333333333333
0.410683602522959, 0.622008467928146, 0.666666666666667 0, 0, 0
virtual_coordinates_stop
connect_virtual JP1 C1 P1
connect_virtual JP1__1 P1 B1__1
connect_virtual JB1__1 B1__1 SUBUNIT
connect_virtual JP1__2 P1 B1__2
connect_virtual JB1__2 B1__2 SUBUNIT
connect_virtual JP1__3 P1 B1__3
connect_virtual JB1__3 B1__3 SUBUNIT
connect_virtual JC2 C1 C2
connect_virtual JP2 C2 P2
connect_virtual JP2__1 P2 B2__1
connect_virtual JB2__1 B2__1 SUBUNIT
connect_virtual JP2__2 P2 B2__2
connect_virtual JB2__2 B2__2 SUBUNIT
connect_virtual JP2__3 P2 B2__3
connect_virtual JB2__3 B2__3 SUBUNIT
connect_virtual JC3 C1 C3
connect_virtual JP3 C3 P3
connect_virtual JP3__1 P3 B3__1
connect_virtual JB3__1 B3__1 SUBUNIT
connect_virtual JP3__2 P3 B3__2
connect_virtual JB3__2 B3__2 SUBUNIT
connect_virtual JP3__3 P3 B3__3
connect_virtual JB3__3 B3__3 SUBUNIT
connect_virtual JC4 C1 C4
connect_virtual JP4 C4 P4
connect_virtual JP4__1 P4 B4__1
connect_virtual JB4__1 B4__1 SUBUNIT
connect_virtual JP4__2 P4 B4__2
connect_virtual JB4__2 B4__2 SUBUNIT
connect_virtual JP4__3 P4 B4__3
connect_virtual JB4__3 B4__3 SUBUNIT
set_dof JP1 x(20.0) angle_x
set_jump_group JGP JP1 JP2 JP3 JP4
set_jump_group JGB JB1__1 JB1__2 JB1__3 JB2__1 JB2__2 JB2__3 JB3__1
JB3__2 JB3__3 JB4__1 JB4__2 JB4__3
```

Figure 2B:
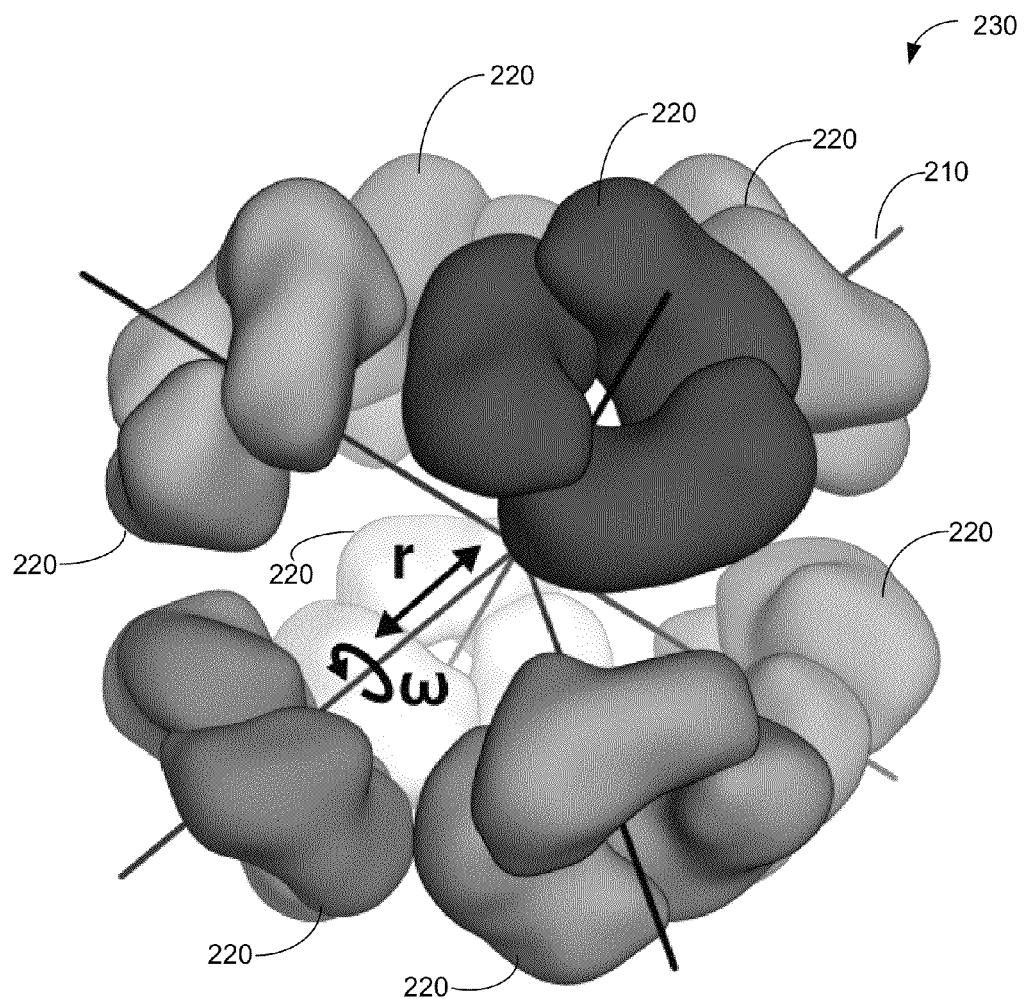
FIG. 2B shows an example docked configuration of the target architecture with multiple copies of a protein building block arranged in a symmetric protein architecture.

FIG. 2B shows an example docked configuration 230 of target architecture 210. In the example shown in FIG. 2B, eight copies of symmetric trimer 220, used as a protein building block, are symmetrically arranged in target architecture 210. The pre-existing organization of oligomeric building block; e.g., trimer 220, fixes several (in this case four) rigid body degrees of freedom (DOFs). Docked configuration 230 includes two additional rigid body degrees of freedom, radial displacement shown as "r" in FIG. 2B, and axial rotation shown as "ω" in FIG. 2B.

Symmetrical docking can be computationally performed by systematically varying radial displacement and axial rotation DOFs. In some embodiments, choices in the DOFs are applied symmetrically to all subunits. Then, a computation can be performed indicating suitability of each configuration for interface design. For example, points corresponding to the docked configuration of FIG. 2B, in which the building blocks are not in contact, correspond to an unsuitable configuration. FIG. 2D shows a highly complementary, and therefore suitable, interface, with each of the building blocks in contact with three other building blocks.

Protein building blocks can be computationally symmetrically docked along the axes of the symmetric architecture. An application was written within the Rosetta macromolecular modeling framework to dock oligomeric protein building blocks into higher order symmetries, searching for docked configurations that yield complementary interfaces suitable for interface design. The application, matdes_dock, takes as input a .pdb file containing a single subunit of a starting structure and a symmetry definition file. The subunits can first be arranged symmetrically at the origin according to the defined symmetry, and then the full space of contacting symmetric configurations are sampled by systematically varying the radial displacement and axial rotation degrees of freedom (DOFs) in the system in increments of, for instance, 1 Å and 1°, respectively. Negative translations may also be sampled (by setting the boolean matdes::dock::neg_r command line option to 1) such that both orientations of the building block (inside/outside) are tested.

Configurations in which backbone or beta carbon atoms from different building blocks clash (distance between backbone amide nitrogen and carbonyl oxygen atoms <=2.6 Å; distance between all other backbone/beta carbon atom pairs <=3.0 Å) are discarded. In each non-clashing configuration, a measure of the suitability of the configuration for design or "designability" can be calculated. An example calculation includes summing a number of beta carbon contacts between building blocks, where a contact is defined as two beta carbon atoms within 10 Å. Other designability calculation can include: use of a computational score function configured to generate a score based on the energy of the contacts between neighboring protein building blocks, or configured to generate a score based on determining an area of contact between at least two protein building blocks of the plurality of protein building blocks.

An example of the command line options used with the matdes_dock application is shown in Table 5 below.

TABLE 5

-database <rosetta_database_path>
-s <input_structure>
-symmetry_definition O3.sym
-matdes::pdbID 3n79
-matdes::prefix O3_
-matdes::num_subs_building_block 3
-matdes::num_subs_total 24
-matdes::dock::neg_r 0

Example Designability Heat Map

Figure 2C:
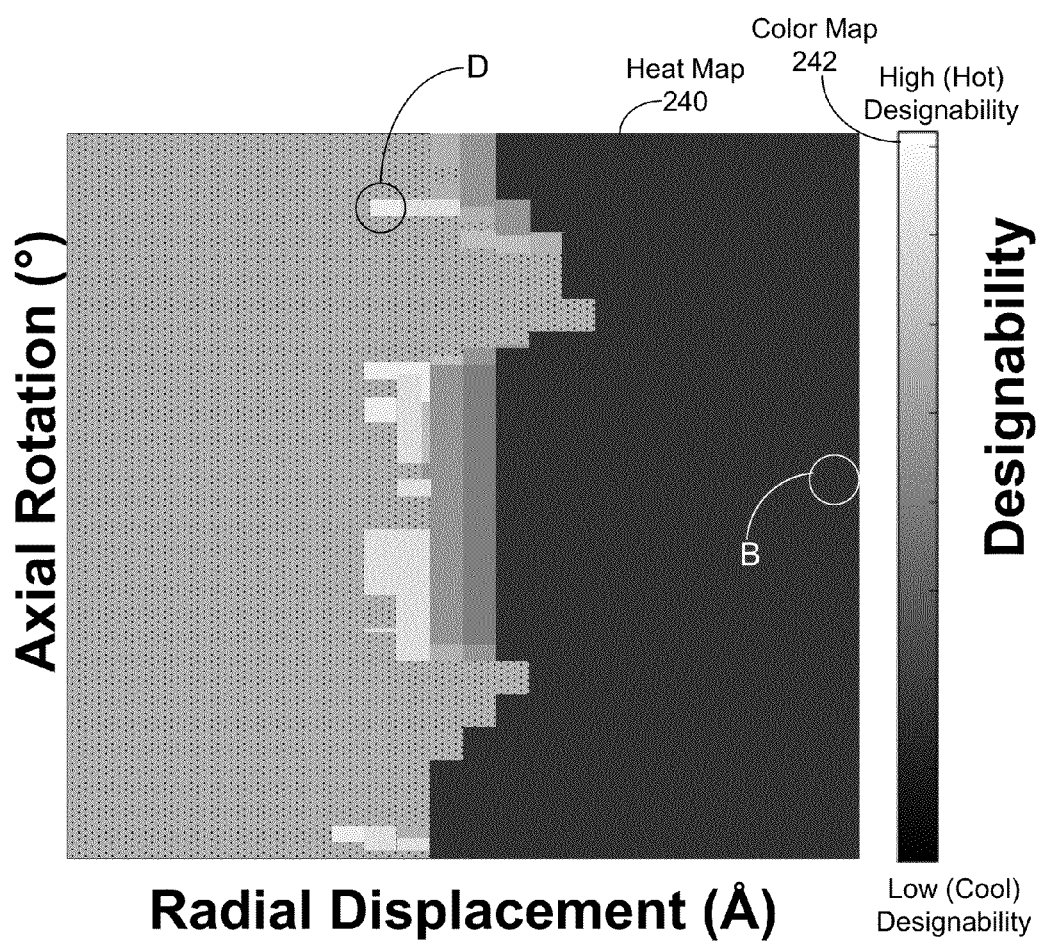
FIG. 2C shows an example heat map relating to designability of a docked configuration for a symmetric protein architecture within pre-determined ranges of radial displacement and axial rotation.
Figure 2D:
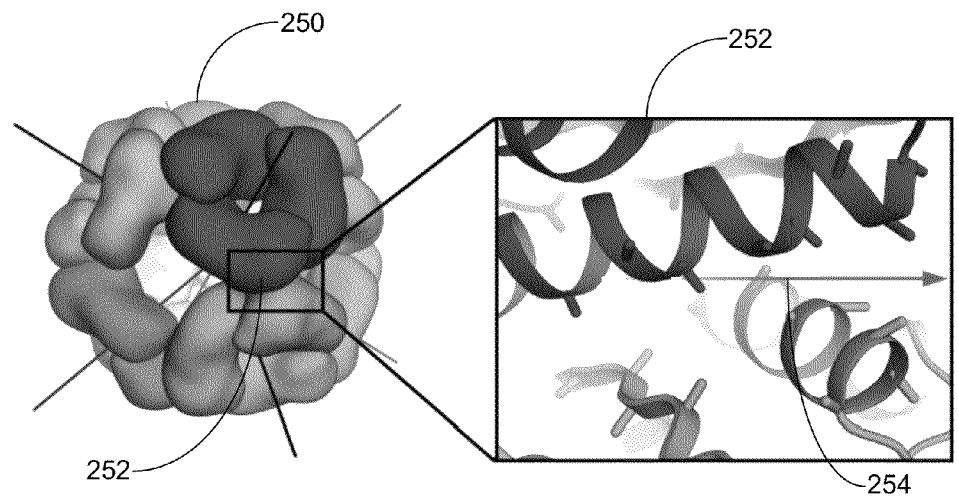
FIG. 2D shows an example interface between protein building blocks within the symmetric protein architecture.

FIG. 2C shows example heat map 240 of designability. Heat map 240 includes two axes corresponding to the two degrees of freedom discussed above: a horizontal axis corresponding to radial displacement in Angstroms (Å) and a vertical axis corresponding to axial rotation in degrees. A designability score can be determined for each protein with a docked configuration with selected values for the radial displacement and axial rotation degrees of freedom. The resulting designability scores can be saved by redirecting the output of a run of the Rosetta software to a log file. The example heat map shown in FIG. 2C is associated with color map 242 indicating a range of gray scale colors from black for "cool" or low designability to white for "hot" or high designability used in heat map 240. Two markers have been added to the head map 240: marker "D" indicating a designability of the docked configuration shown in FIG. 2D (i.e., an example configuration with a high designability) and marker "B" for the designability of the docked configuration shown in FIG. 2B (i.e., an example configuration with a low designability).

A selection of docked configurations for each protein with the highest designability scores or similar measures can be selected for input to a sequence design application. For example, a top 10 (for octahedrally-symmetric designs) or 20 (for tetrahedrally-symmetric designs) docked configurations for each protein based on a number of summed beta carbon contacts, can be input to the sequence design application described immediately below.

Symmetrical Interface Design

In certain embodiments of the present disclosure the interface between the oligomeric protein building blocks is modified to obtain a lower energy conformation. The lower energy conformation can be attained by changing an amino acid sequence at or near the interface. Modifying the interface between oligomeric protein building blocks can be modeled with computer programs, such as, but limited to, programs in the Rosetta software suite.

For example, an application was written within the Rosetta software suite to identify stabilizing mutations at interfaces between oligomeric protein building blocks docked in higher order symmetries. The application, matdes_design, takes as input a .pdb file containing a single subunit of a starting structure and a symmetry definition file. In addition, settings for the two rigid body degrees of freedom (obtained from matdes_dock) are used to specify the initial docked configuration of the subunits. As part of the protocol, a grid of nearby docked configurations centered on the initial configuration can be designed in independent trajectories; the width and number of samples in both dimensions of the grid (radial displacement and axial rotation) can be input as command line options.

In each docked configuration, an amino acid residue within the independent subunit fulfilling four criteria can be selected as a position for mutating or changing during design. One criterion can be that the residue can be at an inter-building block interface, defined as a position in which the beta carbon is within a predetermined cutoff distance to a beta carbon in a different building block; for example, the cutoff distance can be 10 Å. A second criterion can be that the residue is not making inter-subunit contacts within the oligomeric building block; e.g., a determination can be made whether there any atoms within 5 Å of the residue. Residues making intra-building block contacts can be rejected for design, while an exception can be made for a residue making intra-building block contacts that also has a high Rosetta clash (fa_rep) score. A third criterion can be that the residue be determined to have a nonzero solvent accessible surface area in the monomeric state. A fourth criterion can be that interface proline and glycine residues are not designed, but proline side chains are allowed to repack.

Residues passing all four criteria ("design positions") can then be designed using, but not limited to, RosettaDesign while all other residues in the protein remain fixed. FIG. 2D shows an example highly complementary interface 252 including design position 254 shown in detail. A left side image of FIG. 2D shows interface 252 within a dark rectangle superimposed on an example docked target architecture. A right side image of FIG. 2D shows an expanded view of interface 252. Interface 252 lies on an octahedral two-fold symmetry axis 254.

Figure 2E:
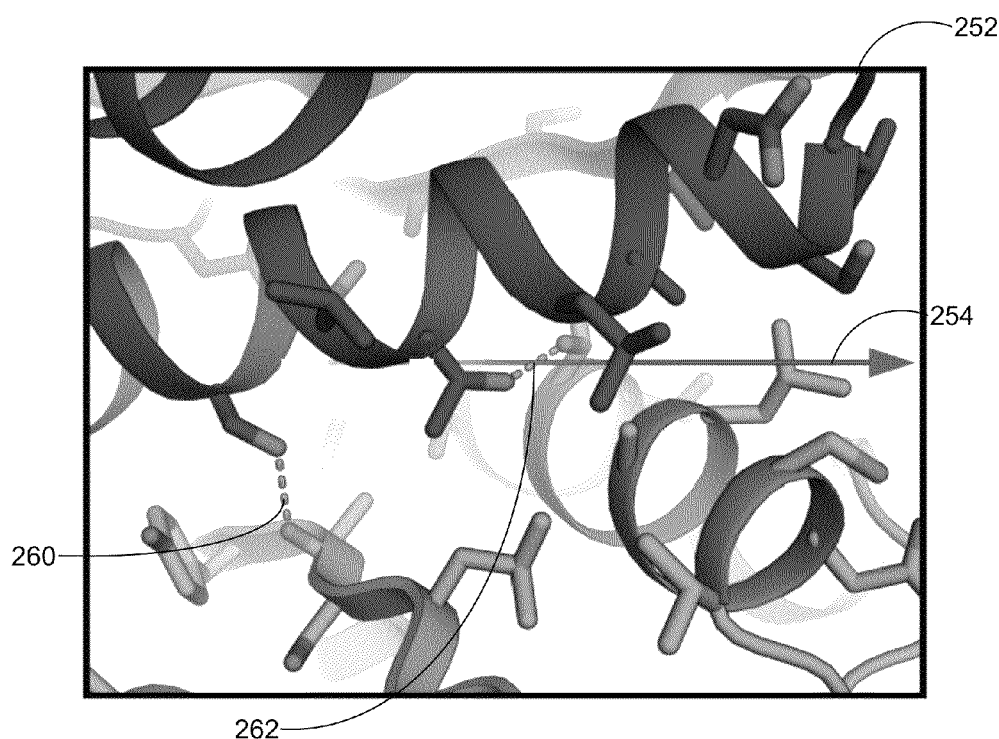
FIG. 2E shows an example designed low-energy protein-protein interface within the symmetric protein architecture.

Symmetric RosettaDesign calculations from programs, such as but not limited to, the Rosetta software suite can be used to design or configure an amino acid sequence for the protein with low-energy, symmetric protein-protein interactions between the trimeric building blocks shown in FIGS. 2B through 2E. FIG. 2E shows designed hydrogen bonds 260, 262 going across the interface 252. The low-energy protein-protein interfaces can drive self-assembly of the desired material.

All design calculations can performed on the independent subunit and propagated symmetrically as described. In some embodiments, a standard Rosetta score function, score12, can be used during design. Once a new sequence for the protein has been designed, configurations for side chains in the design positions can be minimized. Several quality metrics can gauge the quality of the designed interface, including but not limited to: a number of neighboring residues within the monomer for each designed position (e.g., "average degree"), a contacting interface surface area and shape complementarity, a packing score determined by RosettaHoles software, and a predicted binding energy of the interface, defined as the energy of the bound state minus the energy of the unbound state (building block alone) after repacking of the side chains at the design positions.

In a scenario, 55 independent design trajectories were run for each docked configuration of each protein building block. The 55 trajectories sampled the rigid body DOFs in a 2 Å by 2° grid around the starting configuration in 0.1 Å and 0.5° increments. The many thousands of design models for each symmetric architecture can be filtered based on interface size, shape complementarity, and predicted binding energy. Designs that pass these three filters can be analyzed in detail using the above quality metrics in combination with a per-residue measure of the pre-configuration of each designed side chain in the unbound state and a per-residue measure of the change in the predicted binding energy of the complex upon mutation of each designed side chain to alanine During this stage of the design of T3-08, a side chain of arginine 27 can be kept in its native configuration; its guanidinium group can form three side chain-backbone hydrogen bonds within the monomer, two of which cap an adjacent helix, that were deemed important to the stability of the monomer. In some embodiments, a protein folding video game, such as foldit, can interactively test mutations.

An example of the command line options used with the matdes_design application is shown in Table 6 below.

TABLE 6

```
-database <rosetta_database_path>
-s <input_structure>
-symmetry_definition input/T3.sym
-ex1 -ex2
-holes::dalphaball <path_to_DAlphaBall.gcc>
-matdes::num_subs_building_block 3
-matdes::num_subs_total 12
-matdes::prefix T3_
-matdes::pdbID 3ftt
-matdes::radial_disp 32.0
-matdes::angle 110.5
-matdes::design::grid_size_angle 2
-matdes::design::grid_size_radius 2
-matdes::design::grid_nsamp_angle 5
-matdes::design::grid_nsamp_radius 11
```

Polypeptide Assembly Experimental Methods

Amino acid sequences. Point mutants referred to in the main text or FIG. S4 contain no changes from the sequences below other than those indicated by name. The amino acid sequences of the two C-terminal tags used in this study are also presented.

3n79-wt (SEQ ID NO: 7)
MSQAIGILELTSIAKGMELGDAMLKSANVDLLVSKTICPGKFLLMLGGDIG

AIQQAIETGTSQAGEMLVDSLVLANIHPSVLPAISGLNSVDKRQAVGIVETWSVAACISA

ADRAVKGSNVTLVRVHMAFGIGGKCYMVVAGDVSDVNNAVTVASESAGEKGLLVYR

SVIPRPHEAMWRQMVEG

O3-33

(SEQ ID NO: 2)
MSQAIGILELTSIAAGMELGDAMLKSANVDLLVSKTISPGKFLLMLGGDIG

AIQQAIETGTSQAGELLVDSLVLANIHPSVLPAISGLNSVDKRQAVGIVETWSVAACISAA

DRAVKGSNVTLVRVHMAFGIGGKCYMVVAGDVSDVALAVTVASSSAGAYGLLVYAS

LIPRPHEAMWRQMVEG

3ftt-wt (SEQ ID NO: 8)
MTEKEKMLAEKWYDANFDQYLINERARAKDICFELNHTRPSATNKRKELI

DQLFQTTTDNVSISIPFDTDYGWNVKLGKNVYVNTNCYFMDGGQITIGDNVFIGPNCGF

YTATHPLNFHHRNEGFEKAGPIHIGSNTWFGGHVAVLPGVTIGEGSVIGAGSVVTKDIPP

HSLAVGNPCKVVRKIDNDLPSETLNDETIK

T3-08

(SEQ ID NO: 5)
MTEKEKMLAEKWYDANFDQTLINERLRAKVICFALNHTNPSATLKRKVLI

DALFQTTTDNVSISIPFDTDYGWNVKLGKNVYVNTNCYFMDGGQITIGDNVFIGPNCGF

YTATHPLNFHHRNEGFEKAGPIHIGSNTWFGGHVAVLPGVTIGEGSVIGAGSVVTKDIPP

HSLAVGNPCKVVRKIDNDLPSETLNDETIK

T3-1

(SEQ ID NO: 6)
MTEKEKMLAEKWYDANFDQTLINERLRAKVICFALNHTNPVATMMRKVL

IDALFQTTTDNVSISIPFDTDYGWNVKLGKNVYVNTNCYFMDGGQITIGDNVFIGPNCGF

YTATHPLNFHHRNEGFEKAGPIHIGSNTWFGGHVAVLPGVTIGEGSVIGAGSVVTKDIPP

-continued

```
HSLAVGNPCKVVRKIDNDLPSETLNDETIK

A2 tag (for fluorescent labeling)
                                                    (SEQ ID NO: 9)
LEGGDSLDMLEWSL His6 tag
                                                    (SEQ ID NO: 10)
LEHHHHHH
```

Protein Expression, Fluorescent Labeling, and Purification

Codon-optimized genes encoding the designed and corresponding wild-type proteins were constructed from sets of purchased oligonucleotides (Integrated DNA Technologies) by recursive PCR and ligated into the pET29b expression vector (Novagen) using the NdeI and XhoI restriction endonuclease sites. The genes included the A1 peptide tag for fluorescent labeling with the AcpS system at either the N terminus or the C terminus, and all genes ended with a stop codon to prevent translation of the C-terminal (His)$_6$ tag. (His)$_6$-tagged versions of the proteins were constructed by subcloning the genes without the A1 tags or stop codons into pET29b using the NdeI and XhoI restriction sites. Site-directed mutagenesis was performed to generate plasmids for the expression of mutant O3-33 and T3-08 constructs and T3-10.

Expression plasmids were transformed into BL21(DE3) *E. coli* cells. Cells were grown in LB medium supplemented with 50 mg L$^{-1}$ of kanamycin (Sigma) at 37° C. until an OD$_{600}$ of 0.8 was reached. Protein expression was induced by addition of 0.5 mM isopropyl-thio-β-D-galactopyranoside (Sigma) and allowed to proceed for 5 h at 30° C. (O3-33 and T3-08) or 18° C. (T3-10) before cells were harvested by centrifugation.

For fluorescence analysis, cells were lysed by sonication in 25 mM TRIS pH 7.5, 300 mM NaCl, 8.5 mM MgCl$_2$, 1 mM dithiothreitol (DTT) supplemented with 1 mM phenylmethanesulfonyl fluoride, and the lysates cleared by centrifugation. Supernatants were transferred to fresh tubes and the proteins were labeled by the addition of CoA-488 (New England Biolabs) to a final concentration of 5 μM and the *E. coli* acyl carrier protein synthase AcpS (New England Biolabs) to a final concentration of 1 μM. The labeling reaction was allowed to proceed at 37° C. for 30 min, after which the labeled lysates were analyzed by native PAGE or fluorescence SEC. SDS-PAGE of the labeled lysates was performed to determine the extent to which the endogenous *E. coli* proteins were labeled; very little background labeling was observed. Gels were imaged fluorescently using a Fotodyne gel imaging system equipped with appropriate LEDs and filters.

For purification, cells were lysed by sonication in 50 mM TRIS pH 8.0, 250 mM NaCl, 1 mM DTT, 20 mM imidazole supplemented with 1 mM phenylmethanesulfonyl fluoride, and the lysates were cleared by centrifugation and filtered through 0.22 μM filters (Millipore). The designed, mutant, or corresponding wild-type proteins were purified from the filtered supernatants by nickel affinity chromatography on His-Trap HP columns (GE Life Sciences) and eluted using a linear gradient of imidazole (0.02-0.5 M). Fractions containing pure protein of interest were pooled, concentrated, and analyzed directly (FIG. 2, B to H in the main text; see next section) or further fractionated on a Superdex 200 30/100 gel filtration column (GE Life Sciences) using 25 mM TRIS pH 8.0, 150 mM NaCl, 1 mM DTT as running buffer. Gel filtration fractions containing pure protein in the desired assembly state were pooled, concentrated using centrifugal filter devices (Sartorius Stedim Biotech), and stored at room temperature.

Analytical Size Exclusion Chromatography

All analytical SEC was performed on a Superdex 200 30/100 gel filtration column (GE Life Sciences) using 25 mM TRIS pH 8.0, 200 mM NaCl, 1 mM DTT as running buffer. Elution of fluorescently labeled proteins was observed using an Agilent 1260 Infinity Fluorescence Detector equipped with a 8 μL flow cell; the excitation and emission wavelengths were set to 506 nm 550 nm, respectively. Nickel-purified 3n79-wt, O3-33, and O3-33(A167R) were loaded for SEC analysis at a concentration of 0.5 mg mL$^{-1}$; nickel-purified 3 ftt-wt, T3-08, T3-08(A52Q), and T3-10 were loaded at a concentration of 4 mg mL$^{-1}$. It was found that T3-10, when applied to the sizing column immediately after nickel purification, eluted as a mixture of two peaks corresponding to 12 and about 9 subunits; incubation at room temperature or 37° C. gradually decreased the fraction of protein in the 9 mer peak and increased that in the 12 mer peak over a period of days. The data shown in FIG. 2F in the main text was collected after incubating pooled T3-10 nickel fractions at 37° C. for 48 hours. The apparent molecular weights of the designed proteins were estimated by comparison to the corresponding wild-type trimers and a set of globular protein standards.

Analytical Ultracentrifugation

The sedimentation profile of O3-33 was obtained in a buffer of 50 mM potassium phosphate monobasic, 50 mM sodium phosphate dibasic, 25 mM ammonium sulfate, pH 7.5 using a Beckman Proteome XL-I instrument. Two concentrations (4.8 and 2.4 mg mL$^{-1}$) of O3-33 were dialyzed overnight prior to the experiment in order to ensure buffer identity between sample and reference solutions. A sedimentation velocity run was performed using two sector AUC cells with a charcoal-epon centerpiece. 440 μL of sample and reference were loaded into each cell and the cells were centrifuged at 10,000 rpm in an 8-hole rotor. Absorbance at 280 nm was used to monitor the protein. The sample was observed to have fully sedimented to the bottom of the cell in 14 hours; the experiment was allowed to continue for an additional 7 hours to ensure completion. The data was analyzed using a c(s) distribution analysis with the program SEDFIT. A sedimentation distribution from 0 to 200 s was determined using a resolution of 0.4 s. The program SEDNTERP was used to calculate buffer viscosity and density using the information provided.

In the c(s) distribution analysis, the experimental boundary profile was fitted, using both a Simplex and a Marquadt-Levenberg algorithm, to the equation $$a(r,t) = c(s) \cdot \chi 1(s,D,r,t) \cdot ds,$$

where c(s) is the concentration at each value of the sedimentation coefficient in the distribution and $\chi_1(s,D,r,t)$ is the normalized Lamm equation solution for an individual species. Since multiple best fit solutions can result from this analysis the simplest distribution that fits the data was determined by performing a Maximum Entropy regularization of the fit using a 95% confidence level (P-value=0.68). Integration of each peak observed in the c(s) distribution provides the loading signal of that species as well as a precise signal averaged s-value. A molecular weight estimate can be determined by using the recovered sedimentation coefficients corrected for density and viscosity changes at 20° C. in the Svedberg equation, $$sD = M(1-v)RT$$

Where s is the sedimentation coefficient in units of $10^{-13}$ sec, D is the diffusion coefficient (from which the Stokes radius is derived), M is the molar mass, v is the partial specific volume, R is the gas constant, and T is the temperature.

Negative Stain Electron Microscopy (EM)

Samples of purified O3-33 or T3-10 were applied to freshly glow discharged carbon coated 400 mesh copper grids (Ted Pella, Inc.) and stained with 0.075% uranyl formate as described previously. Samples were viewed either on a 100 kV or 120 kV transmission electron microscope (FEI, Hillsboro, Oreg.). Images were recorded using a bottom mount Gatan slow scan charge coupled device camera at a nominal magnification of 28,000× and 70,742× at the specimen level for O3-33 and T3-10, respectively. For averaging, 9,411 unique T3-10 particles were selected using Ximdisp and extracted into 100×100 pixel subframes. The stacked subframes were subjected to several rounds of MSA and MRA using IMAGIC to generate class averages.

Electron Cryo-Microscopy Data Collection and Single Particle Reconstruction.

Vitrified samples of O3-33 were prepared by applying 3 μL of 0.3 mg mL$^{-1}$ protein onto a Quantifoil holey carbon grid, blotting with filter paper, and plunging into liquid ethane using an FEI Vitrobot. Frozen samples were loaded onto a Gatan cryo-holder and inserted into a FEI Tecnai F20 operating at 200 kV equipped with a field emission gun. Images were collected at a nominal magnification of 100,000× using an 8 k×8 k TVIPS F816 camera and UCSFImage, a computer assisted data collection program (courtesy Dr. Yifan Cheng, UCSF). Images were binned four times yielding a pixel size of 2.948 Å pixel$^{-1}$ to achieve faster processing of data. Approximately 42,000 particles were selected from 565 images using Electron Micrograph Utility (cryoem.ucsf.edu). Class averages were determined using five consecutive rounds of MSA (multivariate statistical analysis) and MRA (multireference alignment) in IMAGIC. CTF parameters for each image were determined using ctffind3. An initial model for refinement and three-dimensional reconstruction was generated by calculating a map filtered to 40 Å from the O3-33 design model using the pdb2mrc command in EMAN. Initial parameters were generated during cycles of randomized search and refinement using FREALIGN v8.08 using data binned twice. After initial parameters were determined, consecutive cycles of local refinement and reconstruction with applied octahedral symmetry were carried out until there was no improvement in the alignment. Resolution of the three-dimensional model was determined using the 0.5 cutoff of the Fourier shell correlation curve, which indicated about 20 Å. The reconstructions were normalized using the proc3d command in EMAN. The O3-33 design model was fit into the final electron density map using UCSF Chimera.

Crystallographic Methods

Crystallization of O3-33 in Space Groups R32 and P4.

Initial crystallization screens of the His-tagged protein were set up by the Crystallization Core Facility at UCLA. All crystals were obtained by hanging drop vapor diffusion at room temperature. The protein was in a buffer containing 25 mM TRIS pH 8.0, 150 mM sodium chloride, and 1 mM DTT at a concentration of 28 mg mL$^{-1}$. Crystals of various morphologies appeared within hours under numerous conditions. The conditions for crystals of two different morphologies were optimized.

The best quality crystals obtained were hexagonal plates and belonged to space group R32 (O3-33-R32). The optimized reservoir solution was composed of 0.8 M sodium phosphate monobasic, 1.2 M potassium phosphate dibasic, and 0.1 M sodium acetate pH 4.5. The drop was composed of 0.5 μL of protein, 0.4 μL of reservoir, and 0.1 μL of 0.1M L-proline as an additive (final concentration 10 mM L-proline). The crystals reached full size (0.3×0.3×0.05 mm) in approximately 1 day and diffracted to 2.35 Å. The crystals were cryo-protected by soaking for 2 minutes in 2 M lithium sulfate. The asymmetric unit contained 8 molecules.

A second crystal form appeared as cubes or rectangular blocks and belonged to space group P4 (O3-33-P4). The optimized reservoir solution was composed of 1.0 M sodium chloride, 0.35 M lithium sulfate, and 0.1 M sodium acetate pH 4.5. The drop was composed of 1.5 μL of protein and 1.5 μL of reservoir. The crystals reached full size (0.2×0.2×0.3 mm) in approximately 3 days and diffracted to 3.15 Å. The crystals were cryo-protected by soaking for 30 seconds in 2 M lithium sulfate. The asymmetric unit contained 12 molecules. Analysis of the diffraction pattern from this crystal form indicated the presence of a translocation disorder with translocation vector of 0.500, 0.500, +/−0.4015. The effects of the disorder were diminished using the procedures described in ref. 49.

Crystallization of T3-08

Crystal screening was performed as described for O3-33. The protein was in a buffer containing 25 mM TRIS, pH 8.0, 150 mM sodium chloride, and 1 mM DTT at a concentration of 24 mg mL$^{-1}$. Crystals appeared as trigonal pyramids or bi-pyramids and belonged to space group F23. The reservoir solution was composed of 2.0 M sodium chloride and 0.1 M sodium acetate pH 4.6. The drop was composed of 0.2 μL of protein, 0.2 μL of reservoir. The crystals reached full size (0.2×0.2×0.2 mm) in approximately 2 days and diffracted to 3.35 Å. The crystals were cryo-protected by soaking for 30 seconds in a solution containing 65% reservoir and 35% ethylene glycol. The asymmetric unit contained 1 molecule.

Crystallization of T3-10

Crystal screening was performed as described for O3-33. The protein was in a buffer containing 25 mM Tris, pH 7.5, 150 mM sodium chloride, and 1 mM DTT at a concentration of 9 mg mL$^{-1}$. Crystals appeared as quadrilateral plates and belonged to space group C2. The reservoir solution was composed of 7.5% polyethylene glycol 2000 monomethylether and 0.1 M sodium citrate pH 6.0. The drop was composed of 3 μL of protein, 3 μL of reservoir. The crystals reached full size (0.3×0.3×0.1 mm) in approximately 4 days and diffracted to 2.25 Å. The crystals were cryo-protected by soaking for 30 seconds in a solution containing 65% reservoir and 35% glycerol. The asymmetric unit contained 6 molecules.

Data Collection and Structure Determination

Diffraction data sets were collected from O3-33-R32, O3-33-P4, and T3-08 at the Advanced Photon Source (APS), beamline 24-ID-C, equipped with an ADSC Quantum 315 CCD detector. The data set from the T3-10 crystal was collected at the same facility, but with a Pilatus pixel detector. All data were collected at 100 K at the resolution limits given above. Cryo-protection was performed as described above. Data were collected using 1.0° oscillations. The wavelength of the X-rays used for diffraction data from O3-33-R32, O3-33-P4, T3-08, and T3-10 were 0.9794 Å, 0.9201 Å, 0.9791 Å, and 0.9793 Å, respectively. Data reduction and scaling for O3-33-R32 and T3-10 were performed using DENZO/SCALEPACK. XDS/XSCALE was used to process and scale the remaining data sets.

The crystal structures were determined by molecular replacement using the program PHASER. The search model used for the O3-33 structures was based on PDB entry 3N79, PduT C38S mutant from *Salmonella enterica typhimurium*. The search model used for the T3-08 structure was based on PDB entry 3V4E, galactoside O-acetyltransferase from *Staphylococcus aureus aureus*. The search model for the T3-10 structure was the refined T3-10 structure. The models were refined using REFMAC5 and Buster/TNT with TLS parameterization of domain disorder. After each refinement step, the model was visually inspected in COOT, using both 2Fo-Fc and Fo-Fc difference maps. The models were validated with the following structure validation tools: PROCHECK, ERRAT, and VERIFY3D. Greater than 98% of the residues are within the most favoured and additional allowed regions of the Ramachandran plot for all structures. The O3-33 structures have an additional 1.4% of residues in the generous and disallowed regions, corresponding to well defined areas of the electron density map. The ERRAT scores for O3-33-R32, O3-33-P4, T3-08, T3-10 are 97.8%, 97.8%, 84.2%, and 81.1% respectively, indicating that these percentages of residues fall below the 95% confidence limit of being erroneously modeled. Data collection and refinement statistics are reported in Table S2. The coordinates of the final models and the merged structure factors have been deposited in the Protein Data Bank with PDB codes 3VCD, 4DDF, 4DCL, and 4EGG. All images of protein structures were made using PyMOL.

Figure 3:
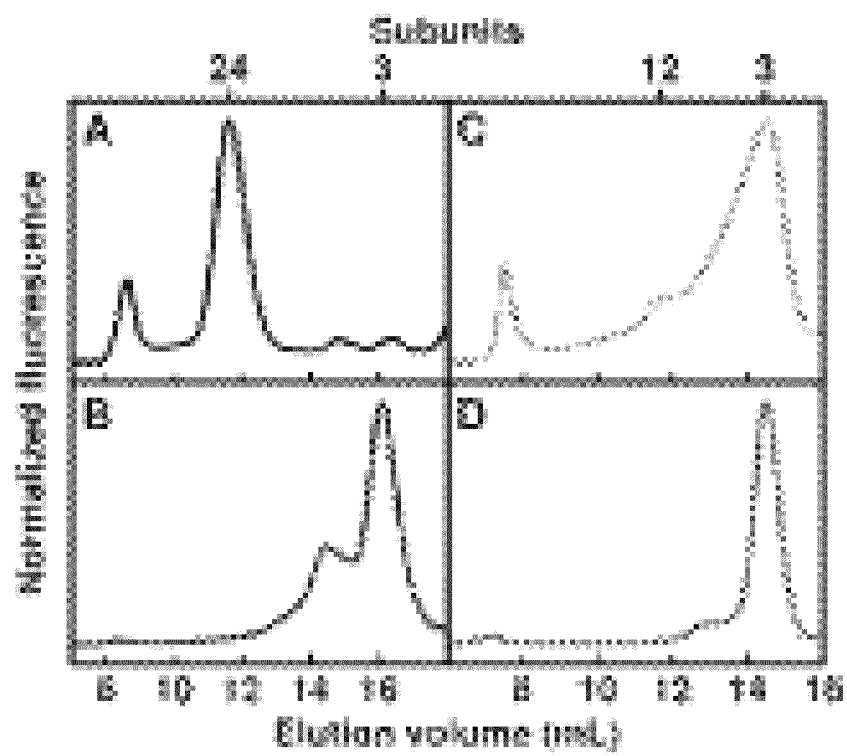
FIG. 3 shows example fluorescent SEC chromatograms.

FIG. 3 shows fluorescent SEC chromatograms of (A) O3-33, (B) 3n79-wt, (C) T3-08, and (D) 3ftt-wt in labeled cell lysates. The chromatograms of the designed proteins reveal peaks at earlier elution volumes than the corresponding wild-type trimers, mirroring the result observed by native PAGE in FIG. 1A of the main text. The elution volumes for the chromatograms in (C) and (D) appear shifted to the left relative to those in (A) and (B) because the column was connected in a different manner such that dead volume before and after the column was minimized; each pair of chromatograms is internally consistent. The data shown in (A) and (B) is used again in FIG. S4 for comparison to several point mutants of O3-33.

Figure 4:
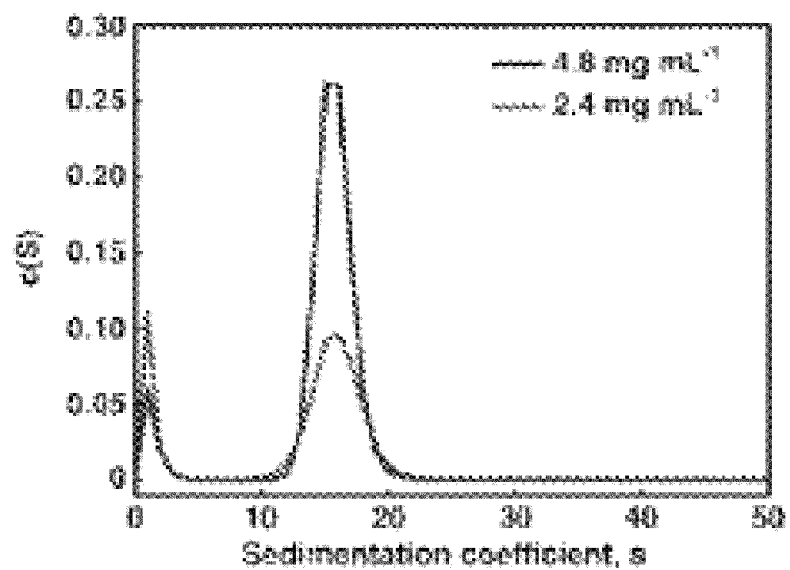
FIG. 4 indicates c(s) distribution of O3-33 at two concentrations.

FIG. 4 indicates c(s) distribution of O3-33 at two concentrations determined using SEDFIT at a resolution of 1.0 s. The distribution for each sample shows a single peak corresponding to an average s of 17.2, yielding a Stokes radius of 7.3 nm for the designed material.

Figure 5:
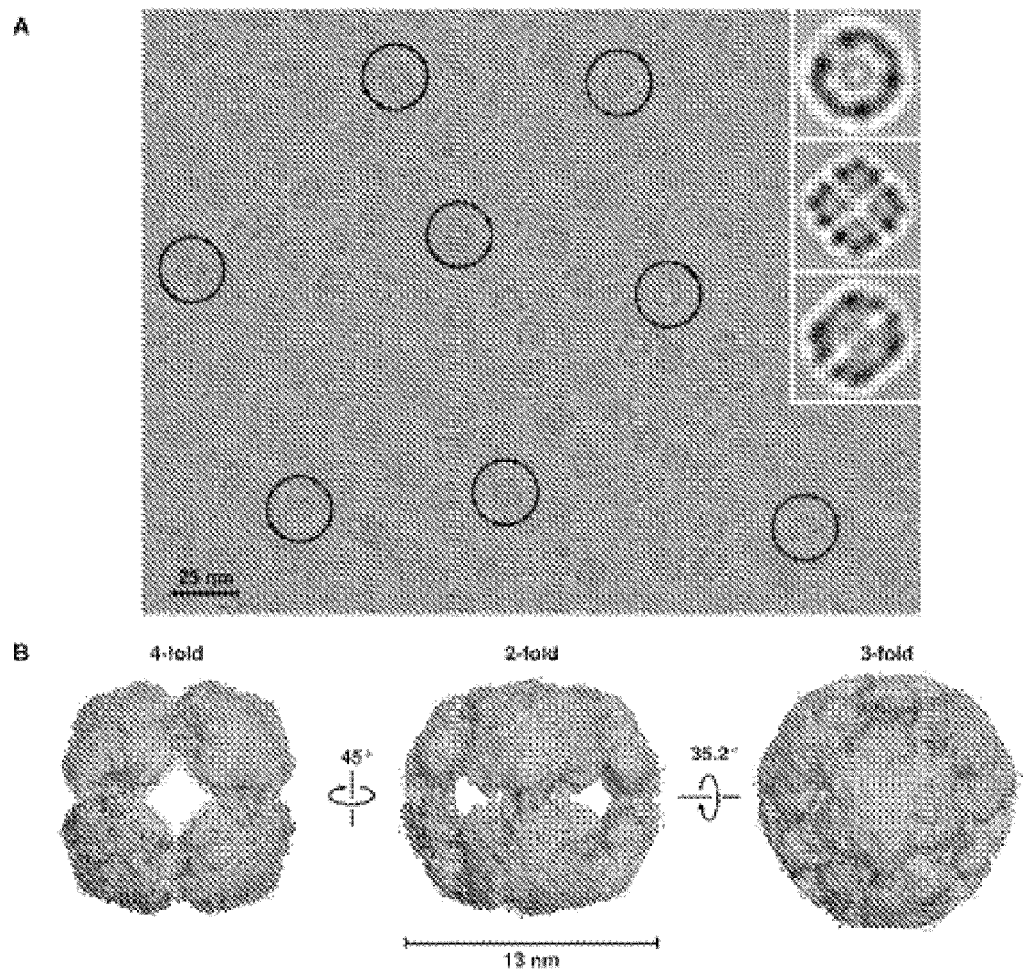
FIG. 5 depicts cryo-electron microscopy of O3-33.

FIG. 5 depicts cryo-electron microscopy of O3-33. (A) Representative electron micrograph of O3-33 frozen in vitrified ice. Inset, three classes of projection averages showing views of the three-fold axis (top), four-fold axis (middle) and two-fold axis (bottom) calculated using the MSA and MRA programs in IMAGIC (42). (B) The density map from the single particle reconstruction is shown as a gray surface with the design model, represented in cartoon, fit into the map.

Figure 6:
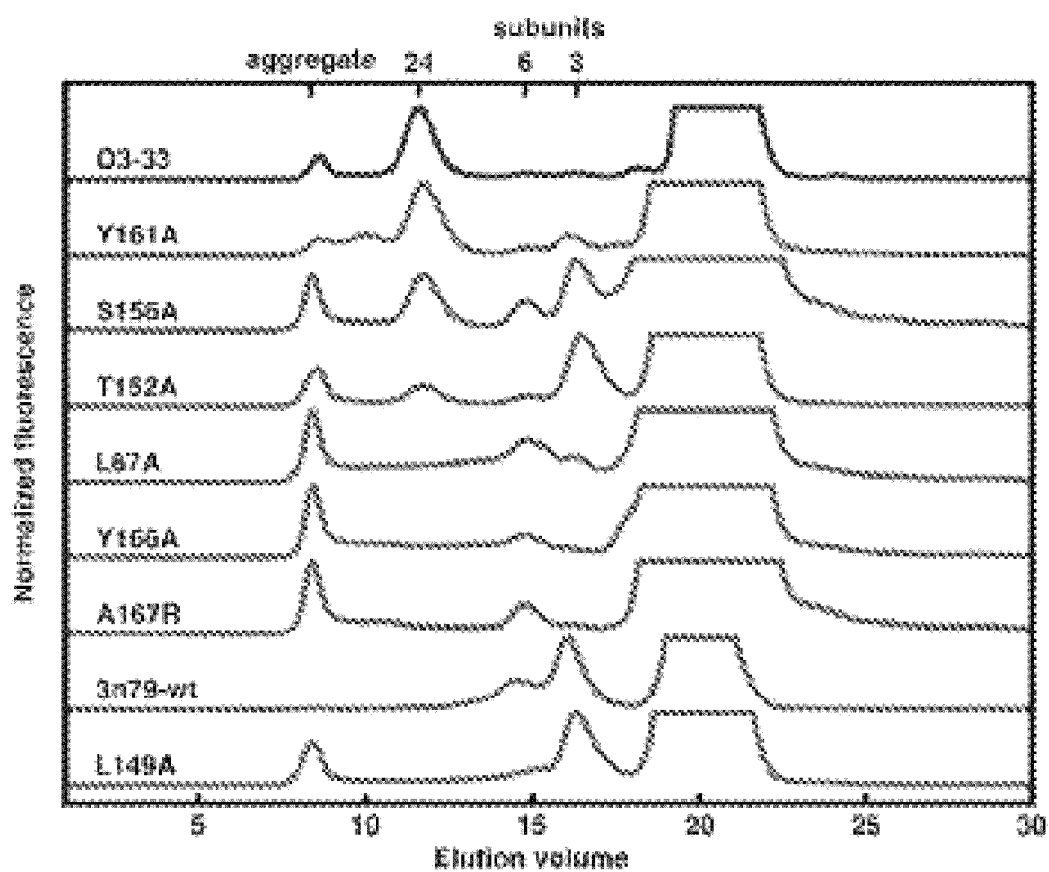
FIG. 6 shows fluorescent SEC chromatograms of 3n79-wt, O3-33, and various interface point mutants in *E. coli* cell lysates.

FIG. 6 shows fluorescent SEC chromatograms of 3n79-wt, O3-33, and various interface point mutants in lysates. Each trace is labeled with the protein name (3n79-wt, O3-33) or the mutation; all mutants are derived from O3-33. The mutations are classified as disrupting or severely disrupting depending on the extent to which they disrupt self-assembly of the designed 24-subunit complex. The plateau-like peak around 20 mL is unbound fluorophore from the labeling reaction saturating the fluorescence detector.

Figure 7:
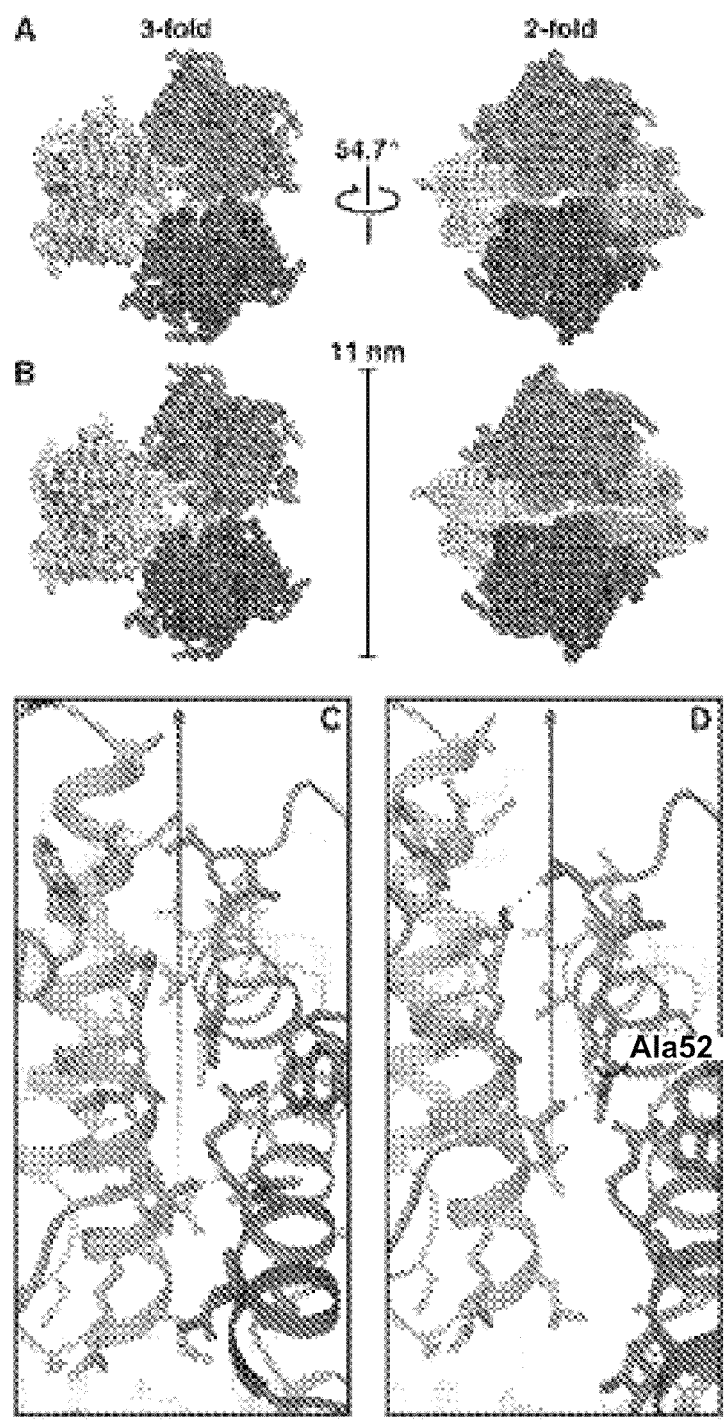
FIG. 7 illustrates a structural characterization of T3-08.

FIG. 7 illustrates a structural characterization of T3-08. Images in (A) and (B) are shown to scale. (A) The T3-08 design model, depicted along its two types of symmetry axes. Each trimeric building block is shown in a different color. (B) The crystal structure of T3-08. (C) The designed interface in the T3-08 design model. (D) The interface in the T3-08 crystal structure. Each trimeric building block is slightly rotated about its three-fold axis relative to the design model, which subtly alters the atomic interactions at the designed interface. The rotation of the building blocks is symmetric and the tetrahedral symmetry of the material is therefore maintained. Alanine 52, which disrupts assembly upon reversion to the wild-type glutamine, is labeled as "Ala52". Images in (C) and (D) are shown from the same viewpoint in separate panels for clarity.

Figure 8:
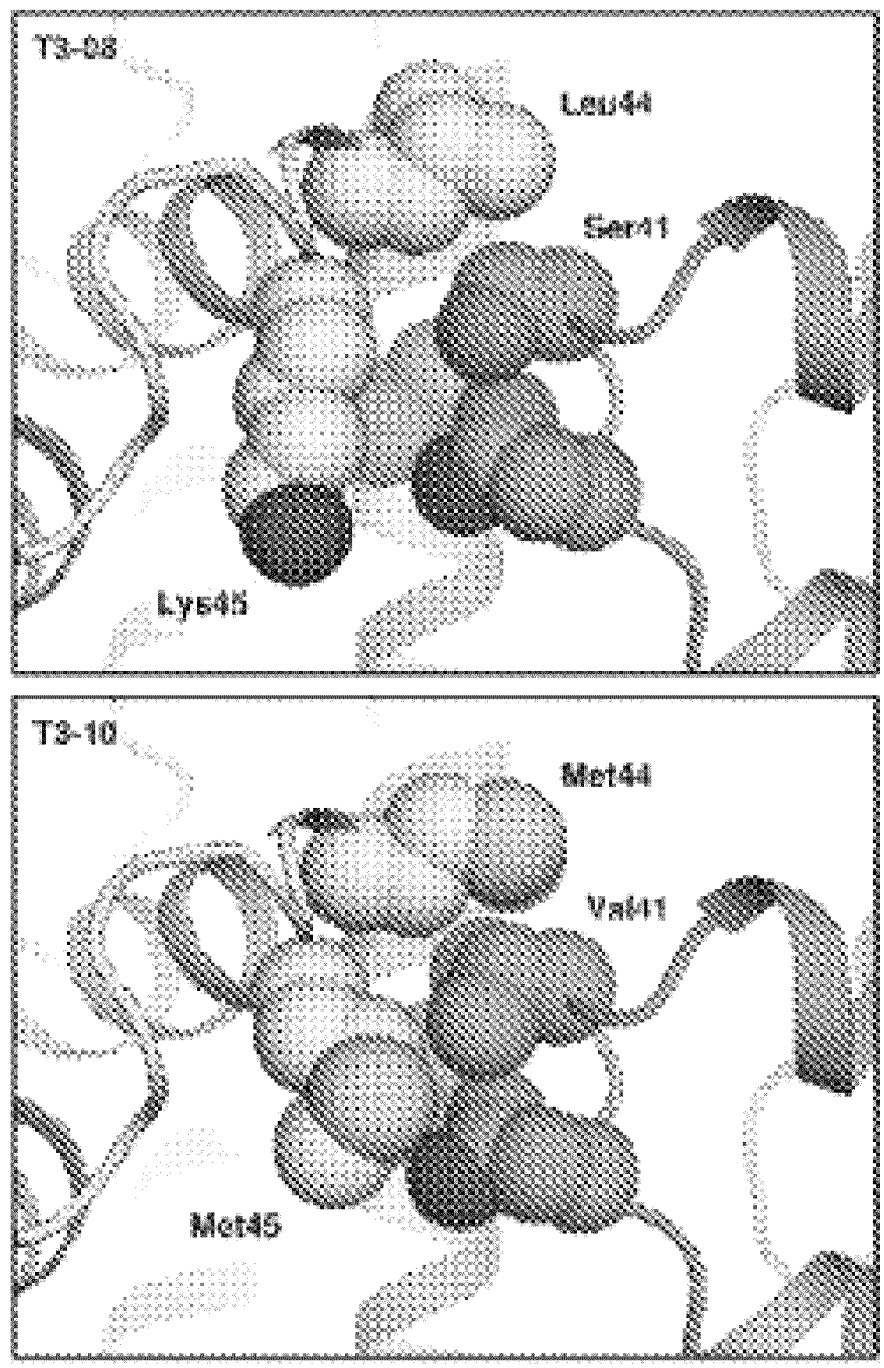
FIG. 8 depicts mutations in T3-10 that stabilize the original designed configuration.

FIG. 8 depicts mutations in T3-10 that stabilize the original designed configuration. The design models of T3-08 (top) and T3-10 (bottom) are shown, focusing on the labeled mutations which result in greater hydrophobic packing across the designed interface.

Table 7 below shows mutations and experimental screening results for all designed proteins.

TABLE 7

| Design name | Scaffold PDB | (#) Mutations* | Soluble expression | Assembly |
|---|---|---|---|---|
| O3-01 | 1h9j | (8) K17Y, D26Y, K34Y, A36V, Q48F, A50W, A51V, K53L | no | N/A |
| O3-02 | 1h9j | (8) K17Y, D26Y, K34A, A36V, Q48F, A50W, A51V, K53L | N/A† | N/A |
| O3-03 | 1nza | (8) Y41F, W43A, E46V, E49A, D50V, K72W, A73L, Y77L | yes | no |
| O3-04 | 1nza | (8) Y41F, W43A, E46V, E49A, D50V, K72A, A73L, Y77L | yes | no |
| O3-05 | 1nza | (10) E13D, Y41F, W43A, Q44N, E46V, E49A, D50V, K72A, A73L, Y77L | yes | no |
| O3-06 | 1qd9 | (12) I14L, E40A, M41L, N43V, D45Y, K47V, D80R, Q83L, E86L, E89L, K112F, D113V | no | N/A |

TABLE 7-continued

| Design name | Scaffold PDB | (#) Mutations* | Soluble expression | Assembly |
|---|---|---|---|---|
| O3-07 | 1ve0 | (6) R15V, D72V, I79R, D81L, D120A, R123E | yes | no |
| O3-08 | 1ve0 | (6) R15V, D72A, I79R, D81L, D120A, R123E | yes | no |
| O3-09 | 1x25 | (12) V13F, R37A, E40A, I41L, V42I, K43I, D45V, K47A, N85D, D86V, A92Y, D113V | yes | no |
| O3-10 | 1x25 | (12) V13F, R37A, E40A, I41L, V42I, K43S, D45V, K47A, N85D, D86V, A92Y, D113V | yes | no |
| O3-11 | 2flz | (11) R11F, D61Y, D87N, V91W, E94F, D96A, R97V, K98V, H99A, E136L, F139A | no | N/A |
| O3-12 | 2flz | (12) R11F, D61Y, D87N, V91W, E94F, D96A, R97V, K98V, H99A, E136L, F139A, T142A | no | N/A |
| O3-13 | 2flz | (8) D76M, Q80S, Q83L, D87F, V91Q, H124Y, E127W, N131A | no | N/A |
| O3-14 | 2flz | (7) D76M, Q80S, Q83L, D87A, V91Q, H124Y, N131A | yes | no |
| O3-15 | 2flz | (8) D76M, Q80A, Q83L, D87F, V91Q, H124Y, E127W, N131A | yes | no |
| O3-16 | 2fvh | (8) R51A, A54L, E55A, R66A, D67N, E71M, E75Y, D88L | no | N/A |
| O3-17 | 2fvh | (9) R29S, R51A, A54L, E55A, R66A, D67S, E71M, E75Y, D88L | no | N/A |
| O3-18 | 2p6c | (8) K14Y, K15I, R16A, E18A, Y73V, D76L, H80Y, D123Y | yes | no |
| O3-19 | 2p6c | (7) K14Y, K15A, R16A, Y73V, D76L, H80Y, D123Y | yes | no |
| O3-20 | 2p6c | (8) K14Y, K15I, R16A, E18A, Y73V, D76L, H80Y, D123Y | yes | no |
| O3-21 | 3jv1 | (9) E74Y, E140I, D180A, D184F, T187Y, S191Y, D197Y, T198A, N201A | yes | no |
| O3-22 | 3jv1 | (10) E54D, E74Y, E140I, D180A, D184F, T187Y, S191Y, D197Y, T198A, N201A | yes | no |
| O3-23 | 3jv1 | (13) R51I, E54D, E74Y, E140I, D180A, H181A, D184F, S185A, T187Y, S191Y, D197Y, T198A, N201A | yes | no |
| O3-24 | 3jv1 | (9) E54I, E74Y, D138A, E140V, D180R, H181L, D184F, T187F, D197Y | no | N/A |
| O3-25 | 3jv1 | (11) E54I, E74Y, D138A, E140V, D180R, H181L, D184F, T187F, D197Y, T198A, N201A | no | N/A |
| O3-26 | 3m1x | (9) D43A, K47V, T48W, E50M, E51A, K85A, V89A, E96L, K115A | no | N/A |
| O3-27 | 3m1x | (8) K47V, T48W, E50M, E51A, K85A, V89A, E96L, K115Y | no | N/A |
| O3-28 | 3m1x | (10) D43A, K47V, T48W, E50M, E51A, K54R, K85A, V89A, E96L, K115A | no | N/A |
| O3-29 | 3n3f | (7) A5L, D11V, K15M, H17I, L18Y, I20Y, D29A | no | N/A |
| O3-30 | 3n3f | (10) A5L, S7Q, D11V, K15M, H17I, L18Y, I20Y, E21S, R28V, D29A | no | N/A |
| O3-31 | 3n79 | (10) K15A, E66A, M67L, N148A, N149L, E156M, E160A, K161Y, R167A, V169L | yes | no |
| O3-32 | 3n79 | (10) K15A, E66D, M67L, N148A, N149L, E156M, E160A, K161Y, R167M, V169L | no | N/A |
| O3-33 | 3n79 | (9) K15A, M67L, N148A, N149L, E156S, E160A, K161Y, R167A, V169L | yes | yes |
| T3-01 | 1qah | (5) Q44L, E52N, N86A, T90L, K116S | yes | no |
| T3-02 | 1qd9 | (8) N43A, K47N, E48I, E82A, Q83S, A85N, R109S, D113A | yes | no |

TABLE 7-continued

| Design name | Scaffold PDB | (#) Mutations* | Soluble expression | Assembly |
|---|---|---|---|---|
| T3-03 | 1x25 | (9) I41L, K43S, K47S, N82A, M83A, S89N, R109A, K112N, D113A | yes | no |
| T3-04 | 1x25 | (9) I41L, K43S, K47S, N82A, M83A, S89N, R109A, K112L, D113A | yes | no |
| T3-05 | 2cwj | (14) V8N, E37A, E38A, F41T, K42A, E43S, D75T, I76A, S77A, R78S, S80N, E81L, A104S, L107N | no | N/A |
| T3-06 | 2flz | (6) D76I, Q110N, R117V, Q121S, E127A, N131A | yes | no |
| T3-07 | 2flz | (7) D76I, Q110N, R117V, Q121S, E127A, N131A, E136D | yes | no |
| T3-08 | 3ftt | (8) Y20T, A26L, D30V, E34A, R39N, N44L, E48V, Q52A | yes | yes |
| T3-09‡ | 3ftt | (9) Y20T, A26L, D30V, E34A, R39N, N44M, K45L, E48V, Q52A | yes | no |
| T3-10‡ | 3ftt | (10) Y20T, A26L, D30V, E34A, R39N, S41V, N44M, K45M, E48V, Q52A | yes | Yes |

*The residue numbers and original amino acid identities listed correspond to the PDB file from which the design was derived. All mutations are at the designed interfaces.
†This design was never tested experimentally.
‡These designs were based off of the T3-08 design model after the T3-08 crystal structure was obtained.

Table 8 below shows example data collection and refinement statistics.

TABLE 8

|  | O3-33-R32 | O3-33-P4 | T3-08 | T3-10 |
|---|---|---|---|---|
| Data collection | | | | |
| Space group | R32 | P4 | F23 | C2 |
| Cell dimensions | | | | |
| a, b, c (Å) | 137.9, 137.9, 560.6 | 169.5, 169.5, 119.9 | 153.7, 153.7, 153.7 | 183.8, 90.8, 207.7 |
| α, β, γ (°) | 90.0, 90.0, 120.0 | 90.0, 90.0, 90.0 | 90.0, 90.0, 90.0 | 90.0, 125.3, 90.0 |
| protomers/asu | 8 | 12 | 1 | 6 |
| Resolution (Å) | 2.35 | 3.15 | 3.35 | 2.25 |
| $R_{merge}$ | 0.066 (0.509)* | 0.101 (0.576) | 0.056 (0.531) | 0.106 (0.553) |
| I/σI | 26.6 (2.4) | 8.7 (1.5) | 24.1 (4.4) | 15.0 (3.0) |
| Completeness (%) | 0.95 (0.89) | 0.98 (0.92) | 0.966 (0.988) | 0.968 (0.934) |
| Redundancy | 6.9 (3.7) | 3.3 (1.9) | 6.7 (6.1) | 6.0 (2.4) |
| Refinement | | | | |
| Resolution (Å) | 2.35 | 3.15 | 3.35 | 2.25 |
| No. reflections | 81,684 | 52,971 | 4,298 | 67,098 |
| $R_{work}/R_{free}$ | 0.180/0.213 | 0.183/0.221 | 0.231/0.240 | 0.208/0.239 |
| No. atoms | | | | |
| Protein | 10,496 | 15,732 | 1,457 | 8,748 |
| Ligand/ion | 506 | 78 | 0 | 48 |
| Water | 375 | 6 | 0 | 297 |
| B-factors (Å$^2$) | | | | |
| Protein | 70.1 | 76.1 | 129.2 | 66.0 |
| Ligand/ion | 78.1 | 114.5 | — | 66.0 |
| Water | 70.1 | 20.4 | — | 57.3 |
| R.m.s. deviations | | | | |
| Bond lengths (Å) | 0.010 | 0.010 | 0.008 | 0.010 |
| Bond angles (°) | 1.2 | 1.3 | 1.1 | 1.1 |

*Highest resolution shell is shown in parentheses.

Example Computing Environment

Figure 9:
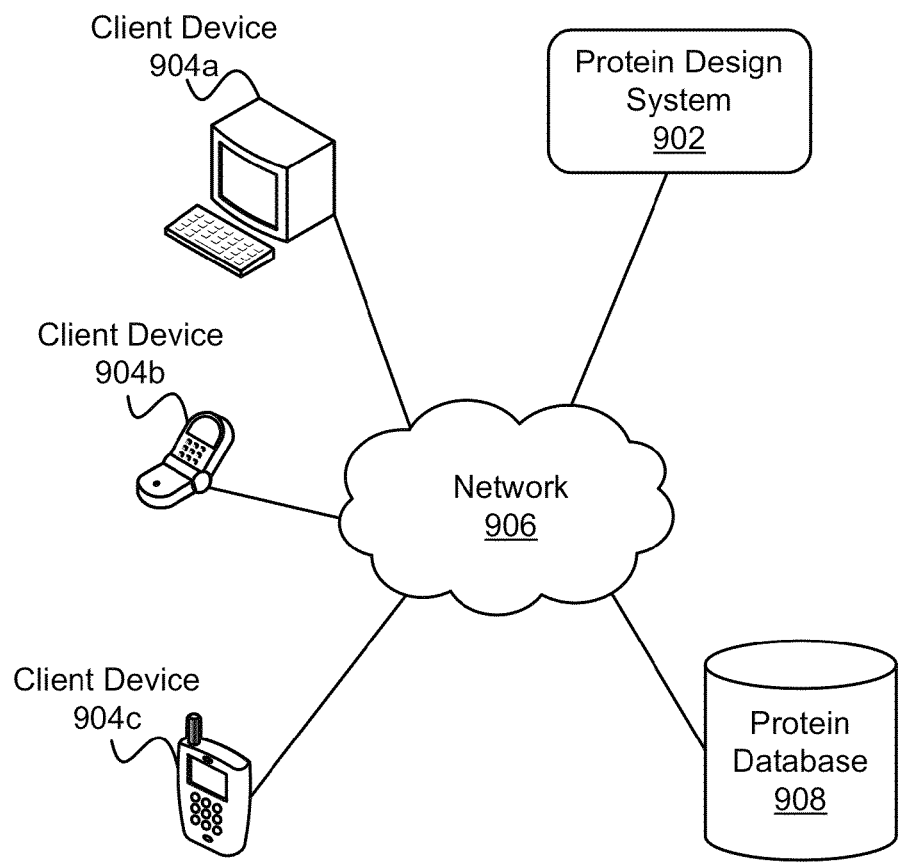
FIG. 9 is a block diagram of an example computing network.

FIG. 9 is a block diagram of an example computing network. Some or all of the above-mentioned techniques disclosed herein, such as but not limited to techniques disclosed as part of and/or being performed by a Rosetta software suite, can be part of and/or performed by a computing device. For example, FIG. 9 shows protein design system 902 configured to communicate, via network 906, with client devices 904a, 904b, and 904c and protein database 908. In some embodiments, protein design system 902 and/or protein database 908 can be a computing device configured to perform some or all of the herein described methods and techniques, such as but not limited to, method 100 and functionality described as being part of or related to the Rosetta software suite. Protein database 908 can, in some embodiments, store information related to and/or used by the Rosetta software suite.

Network 906 may correspond to a LAN, a wide area network (WAN), a corporate intranet, the public Internet, or any other type of network configured to provide a communications path between networked computing devices. Network 906 may also correspond to a combination of one or more LANs, WANs, corporate intranets, and/or the public Internet.

Although FIG. 9 only shows three client devices 904a, 904b, 904c, distributed application architectures may serve tens, hundreds, or thousands of client devices. Moreover, client devices 904a, 904b, 904c (or any additional client devices) may be any sort of computing device, such as an ordinary laptop computer, desktop computer, network terminal, wireless communication device (e.g., a cell phone or smart phone), and so on. In some embodiments, client devices 904a, 904b, 904c can be dedicated to problem solving/using the Rosetta software suite. In other embodiments, client devices 904a, 904b, 904c can be used as general purpose computers that are configured to perform a number of tasks and need not be dedicated to problem solving. In still other embodiments, part or all of the functionality of protein design system 902 and/or protein database 908 can be incorporated in a client device, such as client device 904a, 904b, and/or 904c.

Computing Device Architecture

Figure 10A:
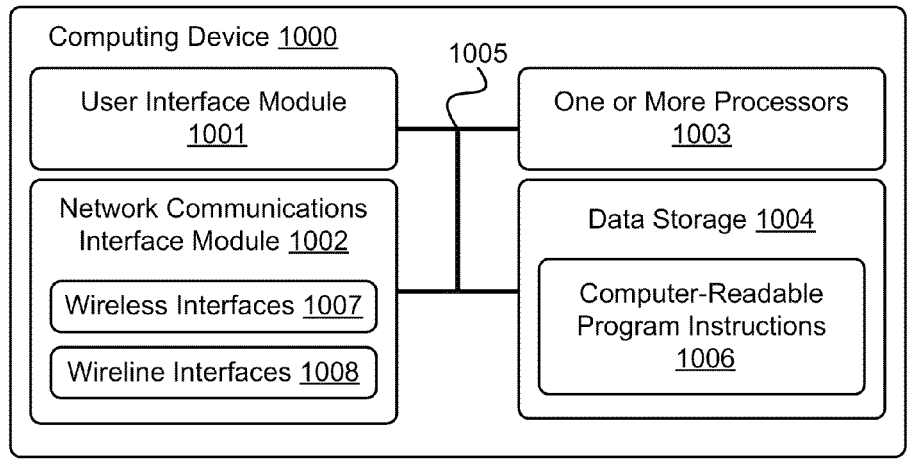
FIG. 10A is a block diagram of an example computing device.

FIG. 10A is a block diagram of an example computing device (e.g., system) In particular, computing device 1000 shown in FIG. 10A can be configured to: include components of and/or perform one or more functions of protein design system 902, client device 904a, 904b, 904c, network 906, and/or protein database 908 and/or carry out part or all of any herein-described methods and techniques, such as but not limited to method 100. Computing device 1000 may include a user interface module 1001, a network-communication interface module 1002, one or more processors 1003, and data storage 1004, all of which may be linked together via a system bus, network, or other connection mechanism 1005.

User interface module 1001 can be operable to send data to and/or receive data from external user input/output devices. For example, user interface module 1001 can be configured to send and/or receive data to and/or from user input devices such as a keyboard, a keypad, a touch screen, a computer mouse, a track ball, a joystick, a camera, a voice recognition module, and/or other similar devices. User interface module 1001 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, either now known or later developed. User interface module 1001 can also be configured to generate audible output(s), such as a speaker, speaker jack, audio output port, audio output device, earphones, and/or other similar devices.

Network-communications interface module 1002 can include one or more wireless interfaces 1007 and/or one or more wireline interfaces 1008 that are configurable to communicate via a network, such as network 906 shown in FIG. 9. Wireless interfaces 1007 can include one or more wireless transmitters, receivers, and/or transceivers, such as a Bluetooth transceiver, a Zigbee transceiver, a Wi-Fi transceiver, a WiMAX transceiver, and/or other similar type of wireless transceiver configurable to communicate via a wireless network. Wireline interfaces 1008 can include one or more wireline transmitters, receivers, and/or transceivers, such as an Ethernet transceiver, a Universal Serial Bus (USB) transceiver, or similar transceiver configurable to communicate via a twisted pair, one or more wires, a coaxial cable, a fiber-optic link, or a similar physical connection to a wireline network.

In some embodiments, network communications interface module 1002 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

Processors 1003 can include one or more general purpose processors and/or one or more special purpose processors (e.g., digital signal processors, application specific integrated circuits, etc.). Processors 1003 can be configured to execute computer-readable program instructions 1006 contained in data storage 1004 and/or other instructions as described herein. Data storage 1004 can include one or more computer-readable storage media that can be read and/or accessed by at least one of processors 1003. The one or more computer-readable storage media can include volatile and/or non-volatile storage components, such as optical, magnetic, organic or other memory or disc storage, which can be integrated in whole or in part with at least one of processors 1003. In some embodiments, data storage 1004 can be implemented using a single physical device (e.g., one optical, magnetic, organic or other memory or disc storage unit), while in other embodiments, data storage 1004 can be implemented using two or more physical devices.

Data storage 1004 can include computer-readable program instructions 1006 and perhaps additional data. For example, in some embodiments, data storage 1004 can store part or all of data utilized by a protein design system and/or a protein database; e.g., protein designs system 902, protein database 908. In some embodiments, data storage 1004 can additionally include storage required to perform at least part of the herein-described methods and techniques and/or at least part of the functionality of the herein-described devices and networks.

Figure 10B:
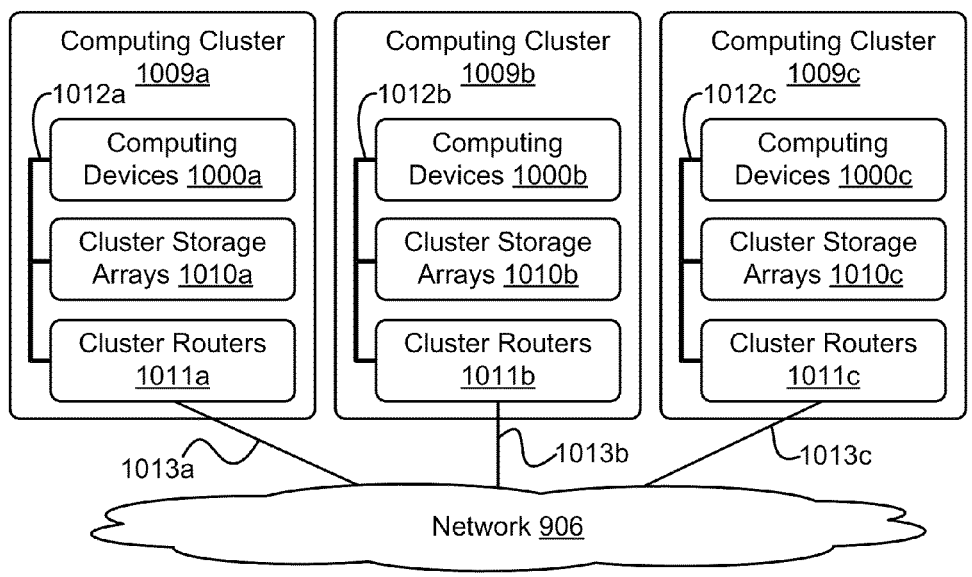
FIG. 10B depicts an example cloud-based server system.

FIG. 10B depicts a network 906 of computing clusters 1009a, 1009b, 1009c arranged as a cloud-based server system in accordance with an example embodiment. Data and/or software for protein design system 902 can be stored on one or more cloud-based devices that store program logic and/or data of cloud-based applications and/or services. In some embodiments, protein design system 902 can be a single computing device residing in a single computing center. In other embodiments, protein design system 902 can include multiple computing devices in a single computing center, or even multiple computing devices located in multiple computing centers located in diverse geographic locations.

In some embodiments, data and/or software for protein design system 902 can be encoded as computer readable information stored in tangible computer readable media (or computer readable storage media) and accessible by client devices 904a, 904b, and 904c, and/or other computing devices. In some embodiments, data and/or software for protein design system 902 can be stored on a single disk drive or other tangible storage media, or can be implemented on multiple disk drives or other tangible storage media located at one or more diverse geographic locations.

FIG. 10B depicts a cloud-based server system in accordance with an example embodiment. In FIG. 10B, the functions of protein design system 902 can be distributed among three computing clusters 1009a, 1009b, and 1008c. Computing cluster 1009a can include one or more computing devices 1000a, cluster storage arrays 1010a, and cluster routers 1011a connected by a local cluster network 1012a. Similarly, computing cluster 1009b can include one or more computing devices 1000b, cluster storage arrays 1010b, and cluster routers 1011b connected by a local cluster network 1012b. Likewise, computing cluster 1009c can include one or more computing devices 1000c, cluster storage arrays 1010c, and cluster routers 1011c connected by a local cluster network 1012c.

In some embodiments, each of the computing clusters 1009a, 1009b, and 1009c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 1009a, for example, computing devices 1000a can be configured to perform various computing tasks of protein design system 902. In one embodiment, the various functionalities of protein design system 902 can be distributed among one or more of computing devices 1000a, 1000b, and 1000c. Computing devices 1000b and 1000c in computing clusters 1009b and 1009c can be configured similarly to computing devices 1000a in computing cluster 1009a. On the other hand, in some embodiments, computing devices 1000a, 1000b, and 1000c can be configured to perform different functions.

In some embodiments, computing tasks and stored data associated with protein design system 902 can be distributed across computing devices 1000a, 1000b, and 1000c based at least in part on the processing requirements of protein design system 902, the processing capabilities of computing devices 1000a, 1000b, and 1000c, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 1010a, 1010b, and 1010c of the computing clusters 1009a, 1009b, and 1009c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of protein design system 902 can be distributed across computing devices 1000a, 1000b, and 1000c of computing clusters 1009a, 1009b, and 1009c, various active portions and/or backup portions of these components can be distributed across cluster storage arrays 1010a, 1010b, and 1010c. For example, some cluster storage arrays can be configured to store one portion of the data and/or software of protein design system 902, while other cluster storage arrays can store a separate portion of the data and/or software of protein design system 902. Additionally, some cluster storage arrays can be configured to store backup versions of data stored in other cluster storage arrays.

The cluster routers 1011a, 1011b, and 1011c in computing clusters 1009a, 1009b, and 1009c can include networking equipment configured to provide internal and external communications for the computing clusters. For example, the cluster routers 1011a in computing cluster 1009a can include one or more internet switching and routing devices configured to provide (i) local area network communications between the computing devices 1000a and the cluster storage arrays 1001a via the local cluster network 1012a, and (ii) wide area network communications between the computing cluster 1009a and the computing clusters 1009b and 1009c via the wide area network connection 1013a to network 906. Cluster routers 1011b and 1011c can include network equipment similar to the cluster routers 1011a, and cluster routers 1011b and 1011c can perform similar networking functions for computing clusters 1009b and 1009b that cluster routers 1011a perform for computing cluster 1009a.

In some embodiments, the configuration of the cluster routers 1011a, 1011b, and 1011c can be based at least in part on the data communication requirements of the computing devices and cluster storage arrays, the data communications capabilities of the network equipment in the cluster routers 1011a, 1011b, and 1011c, the latency and throughput of local networks 1012a, 1012b, 1012c, the latency, throughput, and cost of wide area network links 1013a, 1013b, and 1013c, and/or other factors that can contribute to the cost, speed, fault-tolerance, resiliency, efficiency and/or other design goals of the moderation system architecture.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The above definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The above description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

Numerous modifications and variations of the present disclosure are possible in light of the above teachings.

What is claimed:

1. An isolated polypeptide, comprising the amino acid sequence of SEQ ID NO: 1 capable of forming a multimeric assembly.

2. The isolated polypeptide of claim 1, consisting of the amino acid sequence of SEQ ID NO: 1.

3. The isolated polypeptide of claim 1, comprising the amino acid sequence of SEQ ID NO: 2.

4. A multimeric assembly, comprising a plurality of polypeptides of claim 1.

5. An isolated nucleic acid molecule encoding the isolated polypeptide of claim 1.

6. A nucleic acid expression vector comprising the isolated nucleic acid molecule of claim 5.

7. An isolated recombinant host cell, comprising the nucleic acid expression vector of claim 6.

8. The isolated polypeptide of claim 1, consisting of the amino acid sequence of SEQ ID NO: 2.

9. A multimeric assembly, comprising a plurality of polypeptides of claim 3.

10. An isolated nucleic acid molecule encoding the isolated polypeptide of claim 3.

11. A nucleic acid expression vector comprising the isolated nucleic acid molecule of claim 10.

12. An isolated recombinant host cell, comprising the nucleic acid expression vector of claim 11.

13. A multimeric assembly, comprising a plurality of polypeptides of claim 2.

14. An isolated nucleic acid molecule encoding the isolated polypeptide of claim 2.

15. A nucleic acid expression vector comprising the isolated nucleic acid molecule of claim 14.

16. An isolated recombinant host cell, comprising the nucleic acid expression vector of claim 15.

17. A multimeric assembly, comprising a plurality of polypeptides of claim 8.

18. An isolated nucleic acid molecule encoding the isolated polypeptide of claim 8.

19. A nucleic acid expression vector comprising the isolated nucleic acid molecule of claim 18.

20. An isolated recombinant host cell, comprising the nucleic acid expression vector of claim 19.

* * * * *

SEQUENCE LISTING

```
<160> NUMBER OF SEQ ID NOS: 10

<210> SEQ ID NO 1
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: or any amino acid
<220> FEATURE:
<221> NAME/KEY: MISC_FEATURE
<222> LOCATION: (11)..(11)
```

```
<223> OTHER INFORMATION: or any amino acid
<220> FEATURE:
<221> NAME/KEY: MISC_FEATURE
<222> LOCATION: (25)..(25)
<223> OTHER INFORMATION: or any amino acid
<220> FEATURE:
<221> NAME/KEY: MISC_FEATURE
<222> LOCATION: (28)..(28)
<223> OTHER INFORMATION: or any amino acid
<220> FEATURE:
<221> NAME/KEY: MISC_FEATURE
<222> LOCATION: (30)..(30)
<223> OTHER INFORMATION: or any amino acid
<220> FEATURE:
<221> NAME/KEY: MISC_FEATURE
<222> LOCATION: (35)..(35)
<223> OTHER INFORMATION: or any amino acid
<220> FEATURE:
<221> NAME/KEY: MISC_FEATURE
<222> LOCATION: (38)..(39)
<223> OTHER INFORMATION: or any amino acid
<220> FEATURE:
<221> NAME/KEY: MISC_FEATURE
<222> LOCATION: (41)..(41)
<223> OTHER INFORMATION: or any amino acid
<220> FEATURE:
<221> NAME/KEY: MISC_FEATURE
<222> LOCATION: (49)..(50)
<223> OTHER INFORMATION: or any amino acid
<220> FEATURE:
<221> NAME/KEY: MISC_FEATURE
<222> LOCATION: (55)..(55)
<223> OTHER INFORMATION: or any amino acid
<220> FEATURE:
<221> NAME/KEY: MISC_FEATURE
<222> LOCATION: (68)..(70)
<223> OTHER INFORMATION: or any amino acid
<220> FEATURE:
<221> NAME/KEY: MISC_FEATURE
<222> LOCATION: (75)..(76)
<223> OTHER INFORMATION: or any amino acid
<220> FEATURE:
<221> NAME/KEY: MISC_FEATURE
<222> LOCATION: (78)..(79)
<223> OTHER INFORMATION: or any amino acid
<220> FEATURE:
<221> NAME/KEY: MISC_FEATURE
<222> LOCATION: (83)..(83)
<223> OTHER INFORMATION: or any amino acid
<220> FEATURE:
<221> NAME/KEY: MISC_FEATURE
<222> LOCATION: (86)..(88)
<223> OTHER INFORMATION: or any amino acid
<220> FEATURE:
<221> NAME/KEY: MISC_FEATURE
<222> LOCATION: (90)..(90)
<223> OTHER INFORMATION: or any amino acid
<220> FEATURE:
<221> NAME/KEY: MISC_FEATURE
<222> LOCATION: (92)..(95)
<223> OTHER INFORMATION: or any amino acid
<220> FEATURE:
<221> NAME/KEY: MISC_FEATURE
<222> LOCATION: (103)..(103)
<223> OTHER INFORMATION: or any amino acid
<220> FEATURE:
<221> NAME/KEY: MISC_FEATURE
<222> LOCATION: (114)..(114)
<223> OTHER INFORMATION: or any amino acid
<220> FEATURE:
<221> NAME/KEY: MISC_FEATURE
<222> LOCATION: (117)..(117)
<223> OTHER INFORMATION: or any amino acid
<220> FEATURE:
<221> NAME/KEY: MISC_FEATURE
<222> LOCATION: (120)..(120)
<223> OTHER INFORMATION: or any amino acid
<220> FEATURE:
<221> NAME/KEY: MISC_FEATURE
```

```
<222> LOCATION: (127)..(127)
<223> OTHER INFORMATION: or any amino acid
<220> FEATURE:
<221> NAME/KEY: MISC_FEATURE
<222> LOCATION: (130)..(130)
<223> OTHER INFORMATION: or any amino acid
<220> FEATURE:
<221> NAME/KEY: MISC_FEATURE
<222> LOCATION: (133)..(133)
<223> OTHER INFORMATION: or any amino acid
<220> FEATURE:
<221> NAME/KEY: MISC_FEATURE
<222> LOCATION: (143)..(143)
<223> OTHER INFORMATION: or any amino acid
<220> FEATURE:
<221> NAME/KEY: MISC_FEATURE
<222> LOCATION: (162)..(162)
<223> OTHER INFORMATION: or any amino acid
<220> FEATURE:
<221> NAME/KEY: MISC_FEATURE
<222> LOCATION: (171)..(172)
<223> OTHER INFORMATION: or any amino acid
<220> FEATURE:
<221> NAME/KEY: MISC_FEATURE
<222> LOCATION: (174)..(175)
<223> OTHER INFORMATION: or any amino acid
<220> FEATURE:
<221> NAME/KEY: MISC_FEATURE
<222> LOCATION: (178)..(179)
<223> OTHER INFORMATION: or any amino acid
<220> FEATURE:
<221> NAME/KEY: MISC_FEATURE
<222> LOCATION: (183)..(184)
<223> OTHER INFORMATION: or any amino acid

<400> SEQUENCE: 1

Met Ser Gln Ala Ile Gly Ile Leu Glu Leu Thr Ser Ile Ala Ala Gly
 1               5                  10                  15

Met Glu Leu Gly Asp Ala Met Leu Lys Ser Ala Asn Val Asp Leu Leu
             20                  25                  30

Val Ser Lys Thr Ile Ser Pro Gly Lys Phe Leu Leu Met Leu Gly Gly
         35                  40                  45

Asp Ile Gly Ala Ile Gln Gln Ala Ile Glu Thr Gly Thr Ser Gln Ala
     50                  55                  60

Gly Glu Leu Leu Val Asp Ser Leu Val Leu Ala Asn Ile His Pro Ser
 65                  70                  75                  80

Val Leu Pro Ala Ile Ser Gly Leu Asn Ser Val Asp Lys Arg Gln Ala
                 85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Ser Asp Val Ala Leu Ala Val Thr Val Ala Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly
            180

<210> SEQ ID NO 2
<211> LENGTH: 184
<212> TYPE: PRT
<213> ORGANISM: Artificial Sequence
<220> FEATURE:
```

<223> OTHER INFORMATION: Synthetic

<400> SEQUENCE: 2

Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65              70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Ala Gly Asp Val
    130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly
            180

<210> SEQ ID NO 3
<211> LENGTH: 199
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(9)
<223> OTHER INFORMATION: or any amino acid
<220> FEATURE:
<221> NAME/KEY: MISC_FEATURE
<222> LOCATION: (13)..(13)
<223> OTHER INFORMATION: or any amino acid
<220> FEATURE:
<221> NAME/KEY: MISC_FEATURE
<222> LOCATION: (16)..(16)
<223> OTHER INFORMATION: or any amino acid
<220> FEATURE:
<221> NAME/KEY: MISC_FEATURE
<222> LOCATION: (19)..(19)
<223> OTHER INFORMATION: or any amino acid
<220> FEATURE:
<221> NAME/KEY: MISC_FEATURE
<222> LOCATION: (21)..(21)
<223> OTHER INFORMATION: or any amino acid
<220> FEATURE:
<221> NAME/KEY: MISC_FEATURE
<222> LOCATION: (41)..(41)
<223> OTHER INFORMATION: X is S or V
<220> FEATURE:
<221> NAME/KEY: MISC_FEATURE
<222> LOCATION: (42)..(42)
<223> OTHER INFORMATION: or any amino acid
<220> FEATURE:
<221> NAME/KEY: MISC_FEATURE
<222> LOCATION: (44)..(44)
<223> OTHER INFORMATION: X is L or M

```
<220> FEATURE:
<221> NAME/KEY: MISC_FEATURE
<222> LOCATION: (45)..(45)
<223> OTHER INFORMATION: X is K or M
<220> FEATURE:
<221> NAME/KEY: MISC_FEATURE
<222> LOCATION: (46)..(46)
<223> OTHER INFORMATION: or any amino acid
<220> FEATURE:
<221> NAME/KEY: MISC_FEATURE
<222> LOCATION: (58)..(59)
<223> OTHER INFORMATION: or any amino acid
<220> FEATURE:
<221> NAME/KEY: MISC_FEATURE
<222> LOCATION: (61)..(61)
<223> OTHER INFORMATION: or any amino acid
<220> FEATURE:
<221> NAME/KEY: MISC_FEATURE
<222> LOCATION: (75)..(75)
<223> OTHER INFORMATION: or any amino acid
<220> FEATURE:
<221> NAME/KEY: MISC_FEATURE
<222> LOCATION: (78)..(79)
<223> OTHER INFORMATION: or any amino acid
<220> FEATURE:
<221> NAME/KEY: MISC_FEATURE
<222> LOCATION: (92)..(92)
<223> OTHER INFORMATION: or any amino acid
<220> FEATURE:
<221> NAME/KEY: MISC_FEATURE
<222> LOCATION: (94)..(94)
<223> OTHER INFORMATION: or any amino acid
<220> FEATURE:
<221> NAME/KEY: MISC_FEATURE
<222> LOCATION: (97)..(97)
<223> OTHER INFORMATION: or any amino acid
<220> FEATURE:
<221> NAME/KEY: MISC_FEATURE
<222> LOCATION: (111)..(111)
<223> OTHER INFORMATION: or any amino acid
<220> FEATURE:
<221> NAME/KEY: MISC_FEATURE
<222> LOCATION: (114)..(114)
<223> OTHER INFORMATION: or any amino acid
<220> FEATURE:
<221> NAME/KEY: MISC_FEATURE
<222> LOCATION: (116)..(118)
<223> OTHER INFORMATION: or any amino acid
<220> FEATURE:
<221> NAME/KEY: MISC_FEATURE
<222> LOCATION: (121)..(121)
<223> OTHER INFORMATION: or any amino acid
<220> FEATURE:
<221> NAME/KEY: MISC_FEATURE
<222> LOCATION: (123)..(123)
<223> OTHER INFORMATION: or any amino acid
<220> FEATURE:
<221> NAME/KEY: MISC_FEATURE
<222> LOCATION: (125)..(125)
<223> OTHER INFORMATION: or any amino acid
<220> FEATURE:
<221> NAME/KEY: MISC_FEATURE
<222> LOCATION: (130)..(130)
<223> OTHER INFORMATION: or any amino acid
<220> FEATURE:
<221> NAME/KEY: MISC_FEATURE
<222> LOCATION: (148)..(148)
<223> OTHER INFORMATION: or any amino acid
<220> FEATURE:
<221> NAME/KEY: MISC_FEATURE
<222> LOCATION: (151)..(151)
<223> OTHER INFORMATION: or any amino acid
<220> FEATURE:
<221> NAME/KEY: MISC_FEATURE
<222> LOCATION: (163)..(164)
<223> OTHER INFORMATION: or any amino acid
<220> FEATURE:
<221> NAME/KEY: MISC_FEATURE
<222> LOCATION: (166)..(168)
```

<220> FEATURE:
<221> NAME/KEY: MISC_FEATURE
<222> LOCATION: (172)..(172)
<223> OTHER INFORMATION: or any amino acid
<220> FEATURE:
<221> NAME/KEY: MISC_FEATURE
<222> LOCATION: (175)..(175)
<223> OTHER INFORMATION: or any amino acid
<220> FEATURE:
<221> NAME/KEY: MISC_FEATURE
<222> LOCATION: (177)..(181)
<223> OTHER INFORMATION: or any amino acid
<220> FEATURE:
<221> NAME/KEY: MISC_FEATURE
<222> LOCATION: (183)..(183)
<223> OTHER INFORMATION: or any amino acid
<220> FEATURE:
<221> NAME/KEY: MISC_FEATURE
<222> LOCATION: (185)..(186)
<223> OTHER INFORMATION: or any amino acid

<400> SEQUENCE: 3

Met Thr Glu Lys Glu Lys Met Leu Ala Glu Lys Trp Tyr Asp Ala Asn
1               5                   10                  15

Phe Asp Gln Thr Leu Ile Asn Glu Arg Leu Arg Ala Lys Val Ile Cys
            20                  25                  30

Phe Ala Leu Asn His Thr Asn Pro Xaa Ala Thr Xaa Xaa Arg Lys Val
        35                  40                  45

Leu Ile Asp Ala Leu Phe Gln Thr Thr Thr Asp Asn Val Ser Ile Ser
    50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile His Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Asp Leu Pro Ser Glu Thr
            180                 185                 190

Leu Asn Asp Glu Thr Ile Lys
        195

<210> SEQ ID NO 4
<211> LENGTH: 199
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (41)..(41)
<223> OTHER INFORMATION: X is S or V
<220> FEATURE:
<221> NAME/KEY: MISC_FEATURE
<222> LOCATION: (44)..(44)
<223> OTHER INFORMATION: X is L or M
<220> FEATURE:

```
<221> NAME/KEY: MISC_FEATURE
<222> LOCATION: (45)..(45)
<223> OTHER INFORMATION: X is K or M

<400> SEQUENCE: 4
```

| Met | Thr | Glu | Lys | Glu | Lys | Met | Leu | Ala | Glu | Lys | Trp | Tyr | Asp | Ala | Asn |
|---|---|---|---|---|---|---|---|---|---|---|---|---|---|---|---|
| 1 | | | | 5 | | | | | 10 | | | | | 15 | |

| Phe | Asp | Gln | Thr | Leu | Ile | Asn | Glu | Arg | Leu | Arg | Ala | Lys | Val | Ile | Cys |
|---|---|---|---|---|---|---|---|---|---|---|---|---|---|---|---|
| | | | 20 | | | | | 25 | | | | | 30 | | |

| Phe | Ala | Leu | Asn | His | Thr | Asn | Pro | Xaa | Ala | Thr | Xaa | Xaa | Arg | Lys | Val |
|---|---|---|---|---|---|---|---|---|---|---|---|---|---|---|---|
| | | 35 | | | | | 40 | | | | | 45 | | | |

| Leu | Ile | Asp | Ala | Leu | Phe | Gln | Thr | Thr | Thr | Asp | Asn | Val | Ser | Ile | Ser |
|---|---|---|---|---|---|---|---|---|---|---|---|---|---|---|---|
| 50 | | | | | 55 | | | | | 60 | | | | | |

| Ile | Pro | Phe | Asp | Thr | Asp | Tyr | Gly | Trp | Asn | Val | Lys | Leu | Gly | Lys | Asn |
|---|---|---|---|---|---|---|---|---|---|---|---|---|---|---|---|
| 65 | | | | | 70 | | | | | 75 | | | | | 80 |

| Val | Tyr | Val | Asn | Thr | Asn | Cys | Tyr | Phe | Met | Asp | Gly | Gly | Gln | Ile | Thr |
|---|---|---|---|---|---|---|---|---|---|---|---|---|---|---|---|
| | | | | 85 | | | | | 90 | | | | | 95 | |

| Ile | Gly | Asp | Asn | Val | Phe | Ile | Gly | Pro | Asn | Cys | Gly | Phe | Tyr | Thr | Ala |
|---|---|---|---|---|---|---|---|---|---|---|---|---|---|---|---|
| | | | 100 | | | | | 105 | | | | | 110 | | |

| Thr | His | Pro | Leu | Asn | Phe | His | His | Arg | Asn | Glu | Gly | Phe | Glu | Lys | Ala |
|---|---|---|---|---|---|---|---|---|---|---|---|---|---|---|---|
| | | 115 | | | | | 120 | | | | | 125 | | | |

| Gly | Pro | Ile | His | Ile | Gly | Ser | Asn | Thr | Trp | Phe | Gly | Gly | His | Val | Ala |
|---|---|---|---|---|---|---|---|---|---|---|---|---|---|---|---|
| | 130 | | | | | 135 | | | | | 140 | | | | |

| Val | Leu | Pro | Gly | Val | Thr | Ile | Gly | Glu | Gly | Ser | Val | Ile | Gly | Ala | Gly |
|---|---|---|---|---|---|---|---|---|---|---|---|---|---|---|---|
| 145 | | | | | 150 | | | | | 155 | | | | | 160 |

| Ser | Val | Val | Thr | Lys | Asp | Ile | Pro | Pro | His | Ser | Leu | Ala | Val | Gly | Asn |
|---|---|---|---|---|---|---|---|---|---|---|---|---|---|---|---|
| | | | | 165 | | | | | 170 | | | | | 175 | |

| Pro | Cys | Lys | Val | Val | Arg | Lys | Ile | Asp | Asn | Asp | Leu | Pro | Ser | Glu | Thr |
|---|---|---|---|---|---|---|---|---|---|---|---|---|---|---|---|
| | | | 180 | | | | | 185 | | | | | 190 | | |

| Leu | Asn | Asp | Glu | Thr | Ile | Lys |
|---|---|---|---|---|---|---|
| | | | 195 | | | |

```
<210> SEQ ID NO 5
<211> LENGTH: 199
<212> TYPE: PRT
<213> ORGANISM: Artificial Sequence
<220> FEATURE:
<223> OTHER INFORMATION: Synthetic

<400> SEQUENCE: 5
```

| Met | Thr | Glu | Lys | Glu | Lys | Met | Leu | Ala | Glu | Lys | Trp | Tyr | Asp | Ala | Asn |
|---|---|---|---|---|---|---|---|---|---|---|---|---|---|---|---|
| 1 | | | | 5 | | | | | 10 | | | | | 15 | |

| Phe | Asp | Gln | Thr | Leu | Ile | Asn | Glu | Arg | Leu | Arg | Ala | Lys | Val | Ile | Cys |
|---|---|---|---|---|---|---|---|---|---|---|---|---|---|---|---|
| | | | 20 | | | | | 25 | | | | | 30 | | |

| Phe | Ala | Leu | Asn | His | Thr | Asn | Pro | Ser | Ala | Thr | Leu | Lys | Arg | Lys | Val |
|---|---|---|---|---|---|---|---|---|---|---|---|---|---|---|---|
| | | 35 | | | | | 40 | | | | | 45 | | | |

| Leu | Ile | Asp | Ala | Leu | Phe | Gln | Thr | Thr | Thr | Asp | Asn | Val | Ser | Ile | Ser |
|---|---|---|---|---|---|---|---|---|---|---|---|---|---|---|---|
| 50 | | | | | 55 | | | | | 60 | | | | | |

| Ile | Pro | Phe | Asp | Thr | Asp | Tyr | Gly | Trp | Asn | Val | Lys | Leu | Gly | Lys | Asn |
|---|---|---|---|---|---|---|---|---|---|---|---|---|---|---|---|
| 65 | | | | | 70 | | | | | 75 | | | | | 80 |

| Val | Tyr | Val | Asn | Thr | Asn | Cys | Tyr | Phe | Met | Asp | Gly | Gly | Gln | Ile | Thr |
|---|---|---|---|---|---|---|---|---|---|---|---|---|---|---|---|
| | | | | 85 | | | | | 90 | | | | | 95 | |

| Ile | Gly | Asp | Asn | Val | Phe | Ile | Gly | Pro | Asn | Cys | Gly | Phe | Tyr | Thr | Ala |
|---|---|---|---|---|---|---|---|---|---|---|---|---|---|---|---|
| | | | 100 | | | | | 105 | | | | | 110 | | |

| Thr | His | Pro | Leu | Asn | Phe | His | His | Arg | Asn | Glu | Gly | Phe | Glu | Lys | Ala |
|---|---|---|---|---|---|---|---|---|---|---|---|---|---|---|---|
| | | 115 | | | | | 120 | | | | | 125 | | | |

Gly Pro Ile His Ile Gly Ser Asn Thr Trp Phe Gly Gly His Val Ala
            130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Asp Leu Pro Ser Glu Thr
            180                 185                 190

Leu Asn Asp Glu Thr Ile Lys
        195

<210> SEQ ID NO 6
<211> LENGTH: 199
<212> TYPE: PRT
<213> ORGANISM: Artificial Sequence
<220> FEATURE:
<223> OTHER INFORMATION: Synthetic

<400> SEQUENCE: 6

Met Thr Glu Lys Glu Lys Met Leu Ala Glu Lys Trp Tyr Asp Ala Asn
1               5                   10                  15

Phe Asp Gln Thr Leu Ile Asn Glu Arg Leu Arg Ala Lys Val Ile Cys
            20                  25                  30

Phe Ala Leu Asn His Thr Asn Pro Val Ala Thr Met Met Arg Lys Val
        35                  40                  45

Leu Ile Asp Ala Leu Phe Gln Thr Thr Thr Asp Asn Val Ser Ile Ser
    50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile His Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Asp Leu Pro Ser Glu Thr
            180                 185                 190

Leu Asn Asp Glu Thr Ile Lys
        195

<210> SEQ ID NO 7
<211> LENGTH: 184
<212> TYPE: PRT
<213> ORGANISM: Artificial Sequence
<220> FEATURE:
<223> OTHER INFORMATION: Synthetic

<400> SEQUENCE: 7

Met Ser Gln Ala Ile Gly Ile Leu Glu Leu Thr Ser Ile Ala Lys Gly
1               5                   10                  15

Met Glu Leu Gly Asp Ala Met Leu Lys Ser Ala Asn Val Asp Leu Leu
            20                  25                  30

```
Val Ser Lys Thr Ile Cys Pro Gly Lys Phe Leu Leu Met Leu Gly Gly
        35                  40                  45

Asp Ile Gly Ala Ile Gln Gln Ala Ile Glu Thr Gly Thr Ser Gln Ala
50                  55                  60

Gly Glu Met Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Ser Asp Val Asn Asn Ala Val Thr Val Ala Ser Glu Ser Ala Gly Glu
145                 150                 155                 160

Lys Gly Leu Leu Val Tyr Arg Ser Val Ile Pro Arg Pro His Glu Ala
                165                 170                 175

Met Trp Arg Gln Met Val Glu Gly
            180
```

<210> SEQ ID NO 8
<211> LENGTH: 199
<212> TYPE: PRT
<213> ORGANISM: Artificial Sequence
<220> FEATURE:
<223> OTHER INFORMATION: Synthetic

<400> SEQUENCE: 8

```
Met Thr Glu Lys Glu Lys Met Leu Ala Glu Lys Trp Tyr Asp Ala Asn
1               5                   10                  15

Phe Asp Gln Tyr Leu Ile Asn Glu Arg Ala Arg Ala Lys Asp Ile Cys
                20                  25                  30

Phe Glu Leu Asn His Thr Arg Pro Ser Ala Thr Asn Lys Arg Lys Glu
        35                  40                  45

Leu Ile Asp Gln Leu Phe Gln Thr Thr Thr Asp Asn Val Ser Ile Ser
50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile His Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Asp Leu Pro Ser Glu Thr
            180                 185                 190

Leu Asn Asp Glu Thr Ile Lys
        195
```

-continued

```
<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

Leu Glu Gly Gly Asp Ser Leu Asp Met Leu Glu Trp Ser Leu
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Leu Glu His His His His His His
1               5
```